United States Patent
Betancourt et al.

(10) Patent No.: US 12,350,135 B2
(45) Date of Patent: Jul. 8, 2025

(54) ABSORBENT ARTICLE WITH ODOR CONTROL COMPOSITION

(71) Applicant: The Procter & Gamble Company, Cincinnati, OH (US)

(72) Inventors: Jose Enrique Betancourt, West Chester, OH (US); Chad M. Weldishofer, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 409 days.

(21) Appl. No.: 17/884,082

(22) Filed: Aug. 9, 2022

(65) Prior Publication Data
US 2023/0042590 A1 Feb. 9, 2023

Related U.S. Application Data

(60) Provisional application No. 63/230,879, filed on Aug. 9, 2021.

(51) Int. Cl.
*A61F 13/00* (2024.01)
*A61F 13/15* (2006.01)
*A61F 13/84* (2006.01)
*A61L 15/20* (2006.01)
*A61L 15/48* (2006.01)

(52) U.S. Cl.
CPC .... *A61F 13/8405* (2013.01); *A61F 13/15577* (2013.01); *A61L 15/20* (2013.01); *A61L 15/48* (2013.01); *A61F 2013/8408* (2013.01)

(58) Field of Classification Search
CPC ............ A61F 13/8405; A61F 13/15577; A61F 2013/8408; A61L 15/20; A61L 15/48
See application file for complete search history.

(56) References Cited

U.S. PATENT DOCUMENTS

| | | | | |
|---|---|---|---|---|
| 5,769,832 A | * | 6/1998 | Hasse | A61F 13/581 604/389 |
| 5,942,217 A | * | 8/1999 | Woo | A61K 8/416 424/76.8 |
| 6,960,655 B2 | * | 11/2005 | Di Cintio | A61L 28/0019 604/378 |
| 8,686,215 B2 | * | 4/2014 | Caputi | A61L 15/46 604/367 |
| 9,592,168 B2 | * | 3/2017 | Caputi | A61L 15/46 |
| 9,731,042 B2 | * | 8/2017 | Scavone | A61L 15/46 |
| 10,183,273 B2 | * | 1/2019 | Scavone | A61F 13/49007 |

(Continued)

FOREIGN PATENT DOCUMENTS

WO 9738647 A2 10/1997
WO 2014205047 A1 12/2014
(Continued)

OTHER PUBLICATIONS

PCT Search Report and Written Opinion for PCT/US2022/039805 dated Nov. 28, 2022, 13 pages.

*Primary Examiner* — Guy K Townsend
(74) *Attorney, Agent, or Firm* — Sarah M. DeCristofaro

(57) ABSTRACT

A disposable absorbent article having a topsheet, a backsheet, and an absorbent core disposed between the topsheet and the backsheet is described. The disposable absorbent article includes an odor control composition having a preservative, a surfactant, methylated beta-cyclodextrin (m-BCD), and perfume.

20 Claims, 2 Drawing Sheets

(56) References Cited

U.S. PATENT DOCUMENTS

| | | | |
|---|---|---|---|
| 10,322,032 B2* | 6/2019 | Scavone | A61L 15/46 |
| 10,427,133 B2* | 10/2019 | Scavone | B01J 20/3231 |
| 10,660,984 B2* | 5/2020 | Woo | A61L 9/015 |
| 11,090,250 B2* | 8/2021 | Scavone | A61K 8/738 |
| 11,123,235 B2* | 9/2021 | Bianchi | A61F 13/51113 |
| 11,458,049 B2* | 10/2022 | Sturgis | A61L 15/46 |
| 11,590,254 B2* | 2/2023 | Rezai | B01J 20/3231 |
| 2003/0022573 A1* | 1/2003 | Di Cintio | A61L 28/0019 |
| | | | 428/905 |
| 2010/0324512 A1* | 12/2010 | Caputi | A61L 15/46 |
| | | | 604/359 |
| 2012/0157805 A1* | 6/2012 | Caputi | A61L 15/46 |
| | | | 604/367 |
| 2012/0157946 A1* | 6/2012 | Caputi | A61L 15/28 |
| | | | 604/367 |
| 2012/0226248 A1* | 9/2012 | Caputi | A61L 15/28 |
| | | | 604/359 |
| 2013/0158491 A1* | 6/2013 | Caputi | A61F 13/5611 |
| | | | 604/359 |
| 2014/0180228 A1* | 6/2014 | Caputi | A61F 13/8405 |
| | | | 604/359 |
| 2014/0377207 A1* | 12/2014 | Scavone | A61L 15/20 |
| | | | 424/76.5 |
| 2014/0378920 A1* | 12/2014 | Scavone | A61F 13/00063 |
| | | | 604/359 |
| 2014/0378921 A1* | 12/2014 | Scavone | A61L 15/46 |
| | | | 156/60 |
| 2016/0175214 A1* | 6/2016 | Scavone | A61K 8/42 |
| | | | 132/200 |
| 2017/0165395 A1* | 6/2017 | Scavone | B26B 21/40 |
| 2017/0232135 A1* | 8/2017 | Woo | A61F 13/8405 |
| | | | 604/359 |
| 2017/0368218 A1* | 12/2017 | Scavone | A61L 9/01 |
| 2017/0368532 A1* | 12/2017 | Scavone | A61F 13/49007 |
| 2018/0064588 A1* | 3/2018 | Sturgis | A61F 13/8405 |
| 2018/0333515 A1* | 11/2018 | Rezai | B01J 20/24 |
| 2023/0042590 A1* | 2/2023 | Betancourt | A61F 13/8405 |
| 2024/0115437 A1* | 4/2024 | Betancourt | A61F 13/51113 |

FOREIGN PATENT DOCUMENTS

| | | |
|---|---|---|
| WO | 2014205048 A1 | 12/2014 |
| WO | 2014205053 A1 | 12/2014 |
| WO | 2017223443 A1 | 12/2017 |

* cited by examiner

ABSORBENT ARTICLE WITH ODOR CONTROL COMPOSITION

TECHNICAL FIELD

This application generally relates to absorbent articles comprising improved odor control compositions and methods of making the same.

BACKGROUND

The use of feminine hygiene pads to absorb body exudates has been known for decades. Improvements over the years have addressed the softness/feel of the pad against the skin of the wearer as well as the speed of fluid acquisition, retention of fluid acquisitions and/or fluid capacity of these pads. Another area of improvement for feminine hygiene pads is in the area of odor control.

Odor control compositions for feminine pads are utilized to combat odors generated by the degradation of menstrual fluid and/or urine. While these odor control compositions have proven effective at combating the above odors, their application to the feminine hygiene pads can be, unfortunately, fairly complex.

Many odor control compositions are described as being applied via a solvent carrier. The solvent carrier allows the composition to easily dry on the feminine hygiene article. However, these solvents can increase the complexity of manufacture of feminine hygiene pads. For example, evaporated solvents are often required to be absorbed/abated by a volatile organic compound abatement system. These systems are expensive and can be overly complex to operate. Additionally, these solvents, particularly their vapor, may be flammable. These can increase the risk of fire.

Based on the foregoing, there is a need for an odor control composition which does not require a solvent carrier and facilitates application to feminine hygiene pads.

SUMMARY

Disposable absorbent articles of the present disclosure can provide protection against odors caused by absorbed body exudates on the absorbent article. In one specific example, a disposable absorbent article comprises a topsheet, a backsheet, and an absorbent core disposed between the topsheet and the backsheet, the disposable absorbent article further comprising: an odor control composition comprising a preservative, a surfactant, methylated beta-cyclodextrin (m-BCD), and perfume.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION

Figure 1:
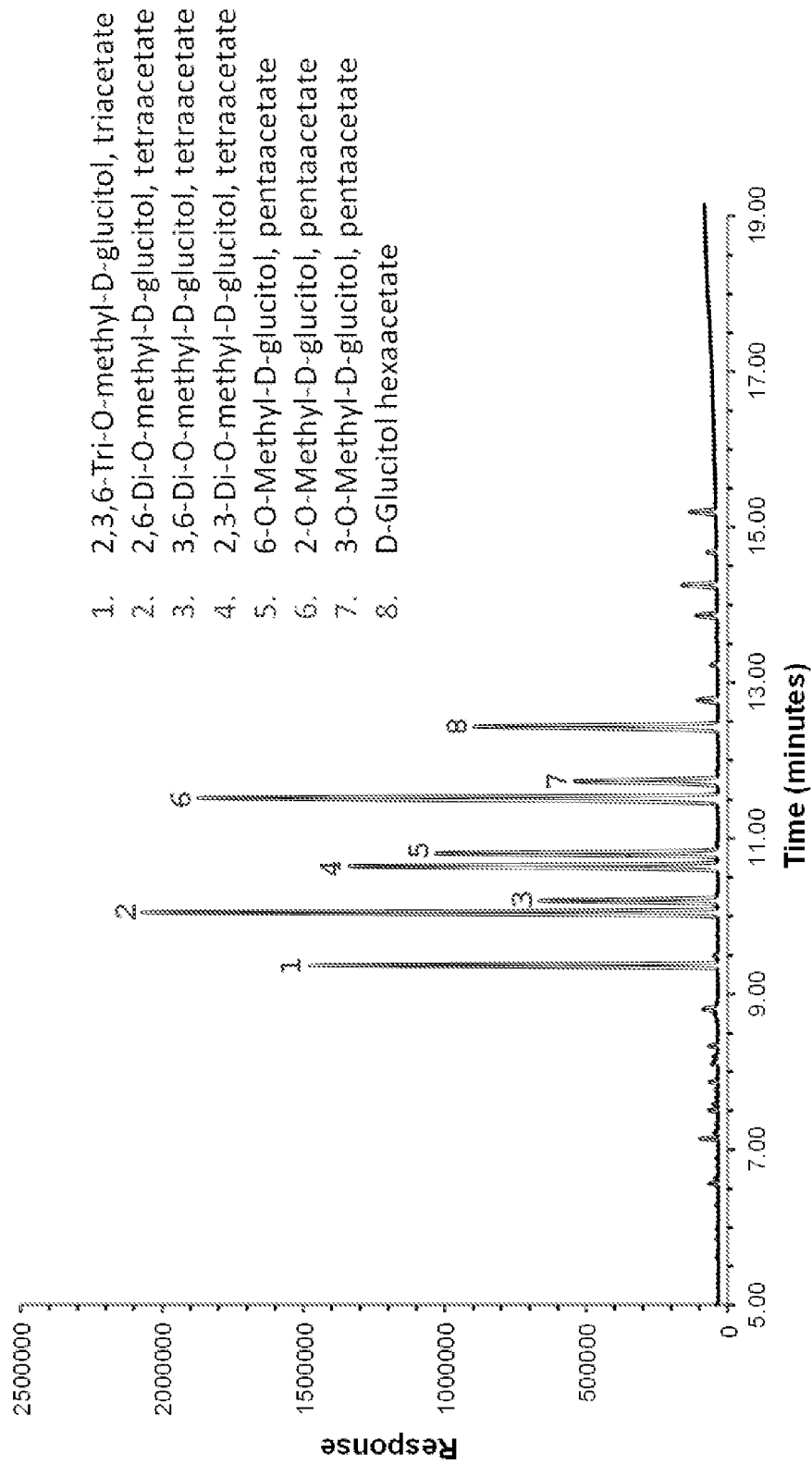
FIG. 1 is a graph depicting a representative chromatogram of hydrolyzed, reduced, and acetylated methyl β-cyclodextrin.

As used herein, the following terms shall have the meaning specified thereafter:

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments (e.g., liners, pads and briefs) and/or feminine hygiene products.

"ClogP" refers to calculated log P values, which is a measure of a compound's hydrophilicity, wherein log P is the octanol water partitioning coefficient as computed by the Consensus algorithm implemented in ACD/Percepta version 14.02 by Advanced Chemistry Development, Inc. (ACD/Labs, Toronto, Canada).

For "complex", it is intended to mean an "inclusion complex" within the meaning of IUPAC Compendium of Chemical Terminology 2nd Edition (1997), wherein the complexing agent (the cyclodextrin in this case) is the host and the complexed compound is the "guest".

"Cyclodextrin complex" refers to a complex of cyclodextrin and perfume.

"Cyclodextrin complex stability constant" or "complex stability constant" (log K) refers to the ability of a perfume raw material to bind to a cyclodextrin. The complex stability constant of a multitude of materials with respect to various cyclodextrins as measured by the calorimetry technique can be found in the literature, for example, Rekharsky and Inoue (1998), Complexation Thermodynamics of Cyclodextrins, Chemical Review, 98, 1875-1917. In addition, for reference, a list of perfume raw materials and their estimated complex stability constants is included in a chart below.

"Molecular weight," unless otherwise designated, refers to the weight average molecular weight which can be calculated by using the sum of the molecular weights of the elements in a molecule. These can be found, for example, in Atomic Weights of the Elements, Weiser, 2005. "Odor Detection Threshold" refers to the lowest concentration in the air of a certain odor compound that is perceivable to the human sense of smell. The Odor detection Threshold of a multitude of materials can be found in vanGemert, L. J.; Odour Thresholds (Compilations of Odour Threshold Values in Air Water and Other Media; Oliemans Punter & Partners; The Netherlands, 2011. It is in units of log molar concentration. In this context, human odor detection thresholds (ODTs) are expressed as olfactory power, or p.ol (the negative log of the molar concentration of the odorant in air at which a human first detects the presence of the odorant). These values can be directly transposed to other commonly used units such as ppm (volume) and ppb (volume): thresholds of 1 ppm and 1 ppb are equivalent to p.ol=6 and p.ol=9, respectively. Odor 30 Detection Threshold can be measured, for example, by the method in International Publication Number WO 2006/138726.

The odor control composition of the present disclosure is an aqueous-based composition and comprises methylated beta cyclodextrin (mBCD), a cyclodextrin compatible surfactant, a preservative, and a fragrance. The odor control composition of the present disclosure allows for reduced complexity during manufacturing as well as reduced risk of use during manufacturing. Moreover, the inventors have surprisingly found that the odor control composition of the present disclosure provided better stability for the disposable absorbent article. It was discovered that disposable absorbent articles comprising a visual signal (colorant disposed on a layer of the disposable absorbent article), and conventional odor control compositions, had an increased likelihood of having their visual signal change appearance due to the odor control composition. However, with the odor control composition of the present disclosure, the visual signals, even over time, remain intact. Additionally, it was similarly discovered that conventional odor control compositions would similarly negatively impact inks disposed on packaging material. For example, inks disposed on a consumer-facing surface of the package material could change in appearance due to the presence of a conventional odor control composition on articles within the package material.

Cyclodextrin-Compatible Surfactants

The cyclodextrin-compatible surfactant provides a low surface tension that permits the composition to spread readily and more uniformly on hydrophobic surfaces. It has been found that the aqueous solution, without such a surfactant, will not spread satisfactorily. The spreading of the composition also allows it to dry faster, so that the treated material is ready to use sooner.

The surfactant for use in providing the required low surface tension in the composition of the present invention should be cyclodextrin-compatible. Namely, the surfactant should not substantially form a complex with the cyclodextrin thereby diminishing performance of the cyclodextrin and/or the surfactant. Complex formation diminishes both the amount of cyclodextrin that can release fragrance and the ability of the surfactant to lower the surface tension of the aqueous composition. Suitable cyclodextrin-compatible surfactants can be readily identified by the absence of effect of cyclodextrin on the surface tension provided by the surfactant. This is achieved by determining the surface tension (in dyne/cm$^2$) of aqueous solutions of the surfactant in the presence and in the absence of about 1% of a specific cyclodextrin in the solutions. The aqueous solutions contain surfactant at concentrations of approximately 0.5%, 0.1%, 0.01%, and 0.005%. The cyclodextrin can affect the surface activity of a surfactant by elevating the surface tension of the surfactant solution. If the surface tension at a given concentration in water differs by more than about 10% from the surface tension of the same surfactant in the 1% solution of the cyclodextrin, that is an indication of a strong interaction between the surfactant and the cyclodextrin. The preferred surfactants herein should have a surface tension in an aqueous solution that is different (lower) by less than about 10%, preferably less than about 5%, and more preferably less than about 1% from that of the same concentration solution containing 1% cyclodextrin.

Nonlimiting examples of cyclodextrin-compatible nonionic surfactants include block copolymers of ethylene oxide and propylene oxide. Suitable block polyoxyethylenepolyoxypropylene polymeric surfactants, that are compatible with most cyclodextrins, include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as C12-18 aliphatic alcohols, are not generally compatible with the cyclodextrin.

Certain of the block polymer surfactant compounds designated Pluronic® and Tetronic® by the BASF-Wyandotte Corp., Wyandotte, Mich., are readily available. Nonlimiting examples of cyclodextrin-compatible surfactants of this type include: Pluronic Surfactants with the general formula H(EO)n(PO)m(EO)nH, wherein EO is an ethylene oxide group, PO is a propylene oxide group, and n and m are numbers that indicate the average number of the groups in the surfactants.

Typical examples of cyclodextrin-compatible Pluronic surfactants are shown in Table 1:

TABLE 1

| Name  | Avg MW | Avg n | Avg m |
|-------|--------|-------|-------|
| L-101 | 3800   | 4     | 59    |
| L-81  | 2750   | 3     | 42    |
| L-44  | 2200   | 10    | 23    |
| L-43  | 1850   | 6     | 22    |
| F-38  | 4700   | 43    | 16    |
| P-84  | 4200   | 19    | 43,   | and mixtures thereof.

Tetronic Surfactants with the general formula:

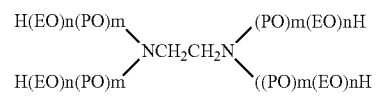

wherein EO, PO, n, and m have the same meanings as above. Typical examples of cyclodextrin-compatible Tetronic surfactants are shown in Table 2:

TABLE 2

| Name | Avg MW | Avg n | Avg m |
|------|--------|-------|-------|
| 901  | 4700   | 3     | 18    |
| 908  | 25000  | 114   | 22,   | and mixtures thereof.

"Reverse" Pluronic and Tetronic surfactants have the following general formulas: Reverse Pluronic Surfactants H(PO)m(EO)n(PO)mH, Reverse Tetronic Surfactants

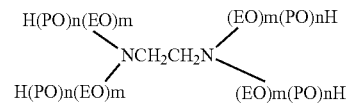

wherein EO, PO, n, and m have the same meanings as above.

Typical examples of cyclodextrin-compatible Reverse Pluronic and Reverse Tetronic surfactants are:

Reverse Pluronic Surfactants in Table 3:

TABLE 3

| Name  | Avg MW | Avg n | Avg m |
|-------|--------|-------|-------|
| 10 R5 | 1950   | 8     | 22    |
| 25 R1 | 2700   | 21    | 6     |

Reverse Tetronic Surfactants in Table 4:

TABLE 4

| Name | Avg MW | Avg n | Avg m |
|---|---|---|---|
| 130 R2 | 7740 | 9 | 26 |
| 70 R2 | 3870 | 4 | 13, | and mixtures thereof.

A preferred class of cyclodextrin-compatible nonionic surfactants are the polyalkyleneoxide polysiloxanes having a dimethyl polysiloxane hydrophobic moiety and one or more hydrophilic polyalkylene side chains and have the general formula:

$R^1$—$(CH_3)_2SiO$—$[(CH_3)_2SiO]a[(CH3)(R^1)SiO]b$-Si$(CH_3)_2$—$R^1$ wherein a+b are from about 1 to about 50, preferably from about 3 to about 30, more preferably from about 10 to about 25, and each R1 is the same or different and is selected from the group consisting of methyl and a poly(ethyleneoxide/propyleneoxide)copolymer group having the general formula:

—$(CH_2)_nO(C_2H_4O)_c(C3H_6O)_dR^2$ with at least one R1 being a poly(ethyleneoxide/propyleneoxide)copolymer group, and wherein n is 3 or 4, preferably 3; total c (for all polyalkyleneoxy side groups) has a value of from 1 to about 100, preferably from about 6 to about 100; total d is from 0 to about 14, preferably from 0 to about 3; and more preferably d is 0; total c+d has a value of from about 5 to about 150, preferably from about 9 to about 100 and each $R^2$ is the same or different and is selected from the group consisting of hydrogen, an alkyl having 1 to 4 carbon atoms, and an acetyl group, preferably hydrogen and methyl group.

Examples of this type of surfactants are the Silwet® surfactants which are available OSi Specialties, Inc., Danbury, Conn. Representative Silwet surfactants are shown in Table 5.

TABLE 5

| Name | Avg MW | Avg a + b | Avg total c |
|---|---|---|---|
| L-7608 | 600 | 1 | 9 |
| L-7607 | 1000 | 2 | 17 |
| L-77 | 600 | 1 | 9 |
| L-7605 | 6000 | 20 | 99 |
| L-7604 | 4000 | 21 | 53 |
| L-7600 | 4000 | 11 | 68 |
| L-7657 | 5000 | 20 | 76 |
| L-7602 | 3000 | 20 | 29 |

The molecular weight of the polyalkyleneoxy group ($R^1$) is less than or equal to about 10,000. Preferably, the molecular weight of the polyalkyleneoxy group is less than or equal to about 8,000, and most preferably ranges from about 300 to about 5,000. Thus, the values of c and d can be those numbers which provide molecular weights within these ranges. However, the number of ethyleneoxy units (—$C_2H_4O$) in the polyether chain ($R^1$) must be sufficient to render the polyalkyleneoxide polysiloxane water dispersible or water soluble. If propyleneoxy groups are present in the polyalkylenoxy chain, they can be distributed randomly in the chain or exist as blocks. Preferred Silwet surfactants are L-7600, L-7602, L-7604, L-7605, L-7657, and mixtures thereof. Besides surface activity, polyalkyleneoxide polysiloxane surfactants can also provide other benefits, such as antistatic benefits, lubricity and softness to fabrics. The preparation of polyalkyleneoxide polysiloxanes is well known in the art. Polyalkyleneoxide polysiloxanes of the present invention can be prepared according to the procedure set forth in U.S. Pat. No. 3,299,112, incorporated herein by reference. Typically, polyalkyleneoxide polysiloxanes of the surfactant blend of the present invention are readily prepared by an addition reaction between a hydrosiloxane (i.e., a siloxane containing silicon-bonded hydrogen) and an alkenyl ether (e.g., a vinyl, allyl, or methallyl ether) of an alkoxy or hydroxy end-blocked polyalkylene oxide). The reaction conditions employed in addition reactions of this type are well known in the art and in general involve heating the reactants (e.g., at a temperature of from about 85° C. to 110° C.) in the presence of a platinum catalyst (e.g., chloroplatinic acid) and a solvent (e.g., toluene).

Nonlimiting examples of cyclodextrin-compatible anionic surfactants are the alkyldiphenyl oxide disulfonate, having the general formula:

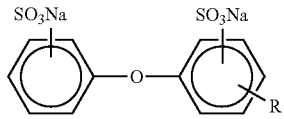

wherein R is an alkyl group. Examples of this type of surfactants are available from the Dow Chemical Company under the trade name Dowfax® wherein R is a linear or branched C6-C16 alkyl group. An example of these cyclodextrin-compatible anionic surfactant is Dowfax 3B2 with R being approximately a linear C10 group. These anionic surfactants are preferably not used when the antimicrobial active or preservative, etc., is cationic to minimize the interaction with the cationic actives, since the effect of both surfactant and active are diminished. The surfactants above are either weakly interactive with cyclodextrin (less than 5% elevation in surface tension, or non-interactive (less than 1% elevation in surface tension). Normal surfactants like sodium dodecyl sulfate and dodecanolpoly(6)ethoxylate are strongly interactive, with more than a 10% elevation in surface tension in the presence of a typical cyclodextrin like hydroxypropyl betacyclodextrin and methylated beta-cyclodextrin.

Typical levels of cyclodextrin-compatible surfactants in usage compositions are from about 0.01% to about 2%, preferably from about 0.03% to about 0.6%, more preferably from about 0.05% to about 0.3%, by weight of the composition, specifically reciting all values within these ranges and any ranges created thereby.

Preservative

The odor control composition further comprises a water-soluble, antimicrobial preservative. As noted previously, cyclodextrin molecules are made up of varying numbers of glucose units which can make them a prime breeding ground for certain microorganisms, especially when in aqueous compositions. This drawback can lead to the problem of storage stability of cyclodextrin solutions for any significant length of time. Contamination by certain microorganisms with subsequent microbial growth can result in an unsightly and/or malodorous solution. Because microbial growth in cyclodextrin solutions is highly objectionable when it occurs, it is highly preferable to include a solubilized, water-soluble, antimicrobial preservative, which is effective for inhibiting and/or regulating microbial growth in order to increase storage stability of the preferably clear, aqueous odor-absorbing solution containing water-soluble cyclodextrin.

It is preferable to use a broad spectrum preservative, e.g., one that is effective on both bacteria (both gram positive and gram negative) and fungi. A limited spectrum preservative, e.g., one that is only effective on a single group of microorganisms, e.g., fungi, can be used in combination with a broad spectrum preservative or other limited spectrum preservatives with complimentary and/or supplementary activity. A mixture of broad spectrum preservatives can also be used. In some cases where a specific group of microbial contaminants is problematic (such as Gram negatives), aminocarboxylate chelators may be used alone or as potentiators in conjunction with other preservatives. These chelators which include, e.g., ethylenediaminetetraacetic acid (EDTA), hydroxyethylenediaminetriacetic acid, diethylenetriaminepentaacetic acid, and other aminocarboxylate chelators, and mixtures thereof, and their salts, and mixtures thereof, can increase preservative effectiveness against Gram-negative bacteria, especially *Pseudomonas* species. Antimicrobial preservatives useful in the odor compositions of the present disclosure include biocidal compounds, i.e., substances that kill microorganisms, or biostatic compounds, i.e., substances that inhibit and/or regulate the growth of microorganisms. Preferred antimicrobial preservatives are those that are water-soluble and are effective at low levels because the organic preservatives can form inclusion complexes with the cyclodextrin molecules and compete with the fragrance molecules for the cyclodextrin cavities, thus limiting the amount of cyclodextrins available to release fragrance. Water-soluble preservatives useful in the present invention are those that have a solubility in water of at least about 0.3 g per 100 ml of water, i.e., greater than about 0.3% at room temperature, preferably greater than about 0.5% at room temperature. These types of preservatives have a lower affinity to the cyclodextrin cavity, at least in the aqueous phase, and are therefore more available to provide antimicrobial activity. Preservatives with a water-solubility of less than about 0.3% and a molecular structure that readily fits into the cyclodextrin cavity, have a greater tendency to form inclusion complexes with the cyclodextrin molecules, thus rendering the preservative less effective to control microbes in the cyclodextrin solution. Therefore, many well-known preservatives such as short chain alkyl esters of p-hydroxybenzoic acid, commonly known as parabens; N-(4-chlorophenyl)-N'-(3,4-dichlorophenyl)urea, also known as 3,4,4'-trichlorocarbanilide or triclocarban; 2,4,4'-trichloro-2'-hydroxy diphenyl ether, commonly known as triclosan are not preferred in the odor control composition of the present disclosure since they are relatively ineffective when used in conjunction with cyclodextrin.

The water-soluble preservative in the odor control composition of the present disclosure is included at an effective amount. The term "effective amount" as herein defined means a level sufficient to prevent spoilage, or prevent growth of inadvertently added microorganisms, for a specific period of time. In other words, the preservative is not being used to kill microorganisms on the surface onto which the composition is deposited in order to eliminate odors produced by microorganisms. Instead, it is preferably being used to prevent spoilage of the cyclodextrin solution in order to increase the shelf-life of the composition.

Preferred levels of preservative are from about 0.5% to about 1.0%, more preferably from about 0.5% to about 0.9%, most preferably from about 0.5% to about 0.8%, by weight of the usage composition, specifically reciting all values within these ranges and any ranges created thereby. Without wishing to be bound by theory, it is believed that below about 0.5 percent by weight of preservative may allow unacceptable levels of microbial growth to occur. And, it is further believed that above about 1.0 percent, the benefit received from additional preservative is greatly diminished.

In order to reserve most of the cyclodextrins for odor control, the cyclodextrin to preservative molar ratio should be greater than about 5:1, preferably greater than about 10:1, more preferably greater than about 50:1, even more preferably greater than about 100:1. The preservative can be any organic preservative material which will not cause damage to any layers of the absorbent article, e.g. topsheet, secondary topsheet, absorbent core, backsheet, etc. via discoloration, coloration, bleaching. Preferred water-soluble preservatives include organic sulfur compounds, halogenated compounds, cyclic organic nitrogen compounds, low molecular weight aldehydes, quaternary ammonium compounds, dehydroacetic acid, phenyl and phenolic compounds, and mixtures thereof.

The following are non-limiting examples of preferred water-soluble preservatives for use in the odor control compositions of the present disclosure.

(A). Organic Sulfur Compounds

Preferred water-soluble preservatives for use in the present invention are organic sulfur compounds. Some nonlimiting examples of organic sulfur compounds suitable for use in the present invention are:

(i) 3-Isothiazolone Compounds

A preferred preservative is an antimicrobial, organic preservative containing 3-isothiazolone groups having the formula:

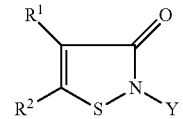

Wherein Y is an unsubstituted alkyl, alkenyl, or alkynyl group of from about 1 to about 18 carbon atoms, an unsubstituted or substituted cycloalkyl group having from about a 3 to about a 6 carbon ring and up to 12 carbon atoms, an unsubstituted or substituted aralkyl group of up to about 10 carbon atoms, or an unsubstituted or substituted aryl group of up to about 10 carbon atoms; $R^1$ is hydrogen, halogen, or a (C1-C4) alkyl group; and $R^2$ is hydrogen, halogen, or a (C1-C4) alkyl group. Preferably, when Y is methyl or ethyl, $R^1$ and $R^2$ should not both be hydrogen.

Salts of these compounds formed by reacting the compound with acids such as hydrochloric, nitric, sulfuric, etc. are also suitable. This class of compounds is disclosed in U.S. Pat. No. 4,265,899, Lewis et al., issued May 5, 1981, and incorporated herein by reference. Examples of said compounds are: 5-chloro-2-methyl-4-isothiazolin-3-one; 2-n-butyl-3-isothiazolone; 2-benzyl-3-isothiazolone; 2-phenyl-3-isothiazolone, 2-methyl-4,5-dichloroisothiazolone; 5-chloro-2-methyl-3-isothiazolone; 2-methyl-4-isothiazolin-3-one; and mixtures thereof. A preferred preservative is a water-soluble mixture of 5-chloro-2-methyl-4-isothiazolin-3-one and 2-methyl-4-isothiazolin-3-one, more preferably a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Company. Other isothiazolins include 1,2-benzisothiazolin-3-one, available under the trade name Proxel® products; and 2-methyl-4,5-trimethylene-4-isothiazolin-3-one, available under the trade name Promexal®. Both Proxel and Promexal are available from Zeneca. They have stability over a wide pH range (i.e., 4-12). These preservatives don't contain active halogens and don't release formaldehyde.

(ii) Sodium Pyrithione

Another preferred organic sulfur preservative is sodium pyrithione, with water solubility of about 50%. Mixtures of the preferred organic sulfur compounds can also be used as the preservative in the present invention.

(B). Halogenated Compounds

Preferred preservatives for use in the present invention are halogenated compounds. Some non-limiting examples of halogenated compounds suitable for use in the odor control composition of the present disclosure are: 5-bromo-5-nitro-1,3-dioxane, available under the trade name Bronidox L® from Henkel. Bronidox L® has a solubility of about 0.46% in water; 2-bromo-2-nitropropane-1,3-diol, available under the trade name Bronopol® from Inolex having a solubility of about 25% in water; 1,1'-hexamethylene bis(5-(p-chlorophenyl) biguanide), commonly known as chlorhexidine, and its salts, e.g., with acetic and gluconic acids can be used as a preservative in the odor control composition of the present disclosure. The digluconate salt is highly water-soluble, about 70% in water, and the diacetate salt has a solubility of about 1.8% in water. Another suitable preservative is 1,1,1,-Trichloro-2-methylpropan-2-ol, commonly known as chlorobutanol, with water solubility of about 0.8%; 4,4'-(Trimethylenedioxy)bis-(3-bromobenzamidine) diisethionate, or dibromopropamidine, with water solubility of about 50%; or mixtures thereof.

(C). Cyclic Organic Nitrogen Compounds

Preferred water-soluble preservatives for use in the odor control composition of the present disclosure are cyclic organic nitrogen compounds. Some non-limiting examples of cyclic organic nitrogen compounds suitable for use in the present invention are:

(i) Imidazolidinedione Compounds

Preferred preservatives for use in the odor control composition of the present disclosure are imidazolidione compounds. Some non-limiting examples of imidazolidinedione compounds suitable for use in the present invention are: 1,3-bis(hydroxymethyl)-5,5-dimethyl-2,4-imidazolidinedione, commonly known as dimethyloldimethylhydantoin, or DMDM hydantoin, available as, e.g., Glydant® from Lonza. DMDM hydantoin has a water solubility of more than 50% in water and is mainly effective on bacteria. When DMDM hydantoin is used, it is preferable that it be used in combination with a broad spectrum preservative such as Kathon CG®, or formaldehyde. A preferred mixture is about a 95:5 DMDM hydantoin to 3-butyl-2-iodopropynylcarbamate mixture, available under the trade name Glydant Plus® from Lonza; N-[1,3-bis(hydroxymethyl)2,5-dioxo-4-imidazolidinyl]-N,N'-bis(hydroxymethyl)urea, commonly known as diazolidinyl urea, available under the trade name Germall II® from Sutton Laboratories, Inc. (Sutton) can be used as the preservative in the odor control composition of the present disclosure; N,N''-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from (Sutton), or mixtures thereof.

(ii) Polymethoxy Bicyclic Oxazolidine

Another preferred water-soluble cyclic organic nitrogen preservative is polymethoxy bicyclic oxazolidine, having the general formula:

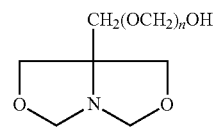

where n has a value of from about 0 to about 5 and is available under the trade name Nuosept® C from Huls America. Mixtures of the preferred cyclic organic nitrogen compounds can also be used as the preservative in the odor control composition of the present disclosure.

(D). Low Molecular Weight Aldehydes (i). Formaldehyde

A preferred preservative for use in the odor control composition of the present disclosure is formaldehyde. Formaldehyde is a broad spectrum preservative which is normally available as formalin which is a 37% aqueous solution of formaldehyde.

(ii) Glutaraldehyde

A preferred preservative for use in the odor control composition of the present disclosure is glutaraldehyde. Glutaraldehyde is a water-soluble, broad spectrum preservative commonly available as a 25% or a 50% solution in water.

(E). Quaternary Compounds

Preferred preservatives for use in the present invention are cationic and/or quaternary compounds. Such compounds include polyaminopropyl biguanide, also known as polyhexamethylene biguanide having the general formula:

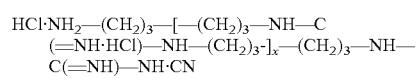

Polyaminopropyl biguanide is a water-soluble, broad spectrum preservative which is available as a 20% aqueous solution available under the trade name Cosmocil CQ® from ICI Americas, Inc., or under the trade name Mikrokill® from Brooks, Inc; 1-(3-Chlorallyl)-3,5,7-triaza-1-azoniaadamantane chloride, available, e.g., under the trade name Dowicil 200 from Dow Chemical, is an effective quaternary ammonium preservative; it is freely soluble in water; however, it has the tendency to discolor (yellow), therefore it is not highly preferred.

Mixtures of the preferred quaternary ammonium compounds can also be used as the preservative in the odor control compositions of the present disclosure.

(F). Dehydroacetic Acid

A preferred preservative for use in the present invention is dehydroacetic acid. Dehydroacetic acid is a broad spectrum preservative preferably in the form of a sodium or a potassium salt so that it is water-soluble. This preservative acts more as a biostatic preservative than a biocidal preservative.

(G). Phenyl and Phenolic Compounds

Some non-limiting examples of phenyl and phenolic compounds suitable for use in odor control compositions of the present disclosure are: 4,4'-diamidino-a,w-dip henoxypropane diisethionate, commonly known as propamidine isethionate, with water solubility of about 16%; and 4,4'-diamidino-α,ω-diphenoxyhexane diisethionate, commonly known as hexamidine isethionate. Other examples are benzyl alcohol, with a water solubility of about 4%.

Additional suitable preservatives for the compositions of the present disclosure may consist of or include one or more compounds represented by the following Structure (I):

wherein R is a substituted or unsubstituted phenyl group or a substituted or unsubstituted phenoxy group. For example, R may be either an unsubstituted phenyl group or an unsubstituted phenoxy group. Mixtures of compounds represented by Structure (I) may also be used.

Thus, either or both of 2-phenoxyethanol, with a water solubility of about 2.67%, and 2-phenylethanol, with a water solubility of about 2%, may be used as preservatives in the composition of the present disclosure. 2-Phenoxyethanol is also known as ethylene glycol phenyl ether; ethylene glycol monophenyl ether; and 1-hydroxy-2-phenoxyethane, and may be obtained as DOWANOL PhE, DOWANOL EPh. or DOWANOL EP from various commercial sources. 2-Phenylethanol is also known as phenylethanol; 2-phenylethan-1-ol; phenethyl alcohol; β-hydroxyethylbenzene; phenylethyl alcohol; β-phenylethanol; and benzyl carbinol and may be obtained from various commercial sources.

(H). Mixtures Thereof

The preservatives of the present invention can be used in mixtures in order to control a broad range of microorganisms. Bacteriostatic effects can sometimes be obtained for aqueous compositions by adjusting the composition pH to an acid pH, e.g., less than about pH 4, preferably less than about pH 3, or a basic pH, e.g., greater than about 10, preferably greater than about 11. Low pH for microbial control is not a preferred approach in the present invention because the low pH can cause chemical degradation of the cyclodextrins. High pH for microbial control is also not preferred because at high pH's, e.g., greater than about 10, preferably greater than about 11, the cyclodextrins can be ionized and their ability to complex with organic materials is reduced. Therefore, aqueous compositions of the odor control composition of the present disclosure should have a pH of from about 3 to about 10, preferably 5 from about 4 to about 8, more preferably from about 4.5 to about 6. The pH can be adjusted with inorganic molecules to minimize complexation with cyclodextrin.

Perfume Compositions

The odor control composition of the present disclosure also comprises a perfume composition. The perfume composition comprises perfume raw materials which may be provided in a carrier. The carrier may be any suitable material including dipropylene glycol and isopropyl myristate. However, the inventors have surprisingly found that the use of dipropylene glcycol as a carrier can negatively impact a visual signal on the absorbent article over time and/or inks disposed on a consumer-facing surface of package material in which absorbent articles are disposed. In contrast, the inventors have surprisingly found the isopropyl myristate does not have the same effect. So, isopropyl myristate may be utilized as the carrier for the raw materials of the perfume composition.

At least a portion of the perfume raw materials may have a complex stability constant of about 3.0 or less; about 2.5 or less, about 2.0 or less, about 1.0 or less, to about 0, to about −1, to about −2, or any combination thereof. Some of the perfume raw material may have a cLogP of about 2.5 or less, about 2.0 or less, about 1.5 or less, about 1.0 or less, to about −3. Some of the perfume raw materials may have a weight average molecular weight of about 200 Daltons or less, about 180 Daltons or less, about 150 Daltons or less, about 100 Daltons or less, to about 50 Daltons. A perfume raw material will have an odor detection threshold. At least a portion of the perfume raw materials in a perfume composition will have an odor detection threshold of about 7-log molar concentration or greater; about 8-log molar concentration or greater; about 9-log molar concentration or greater; to about 11.5-log molar concentration.

The perfume composition comprises about 10% or more, by weight of the perfume, of perfume raw materials which have a complex stability constant of about 3.0 or less, a cLogP of about 2.5 or less, and a weight average molecular weight of about 200 Daltons or less. Going further, the perfume composition may comprise about 20% or more; about 30% or more; about 40% or more, or about 50% or more, up to 100%; of perfume raw materials which have a complex stability constant of about 3.0 or less, a cLogP of about 2.5 or less, and a weight average molecular weight of about 200 Daltons or less. In addition, a perfume composition may also include perfume raw materials with an odor detection threshold of about 7-log molar concentration. A representative, non-limiting, list of perfume raw materials that have a complex stability constant of about 3.0 or less, a cLogP of about 2.5 or less, and a weight average molecular weight of about 200 Daltons or less is included in the Table 6 below.

TABLE 6

| CAS Number | Name | LogP (v3.0) | Formula Weight | Odor Detection Threshold, Neural Net model | bCD Complex Stability Constant |
|---|---|---|---|---|---|
| 10031-96-6 | eugenyl formate | 2.35 | 192.21 | 8.84 | 2.71 |
| 100-52-7 | Benzaldehyde | 1.4 | 106.12 | 7.45 | 2.19 |
| 10094-40-3 | 2-hexen-1-yl acetate | 2.21 | 142.20 | 8.20 | 1.45 |
| 101-39-3 | alpha-methyl cinnamaldehyde | 2.18 | 146.19 | 8.83 | 1.08 |
| 101-41-7 | Methyl phenylacetate | 1.89 | 150.18 | 8.02 | 2.14 |
| 101-48-4 | Viridine (PADMA) | 1.65 | 166.22 | 8.01 | 2.26 |
| 101-97-3 | Ethyl 2-phenylacetate | 2.39 | 164.20 | 8.63 | 2.25 |
| 103-25-3 | methyl hydrocinnamate | 2.04 | 164.20 | 8.20 | 2.24 |
| 103-26-4 | Methyl cinnamate | 2.44 | 162.19 | 8.97 | 2.07 |
| 103-45-7 | 2-Phenylethyl acetate | 2.07 | 164.20 | 8.15 | 1.54 |
| 103-54-8 | Cinnamyl acetate | 2.49 | 176.22 | 8.51 | 1.53 |
| 104-09-6 | lilac acetaldehyde | 2.12 | 134.18 | 9.36 | 2.67 |
| 104-20-1 | 4-(p-Methoxyphenyl)-2-butanone (frambinone) | 1.88 | 178.23 | 8.86 | 1.72 |
| 104-46-1 | Anethole | 2.43 | 148.20 | 8.79 | 2.34 |
| 104-50-7 | gamma-Octalactone | 2.06 | 142.20 | 8.30 | 2.94 |

TABLE 6-continued

| CAS Number | Name | LogP (v3.0) | Formula Weight | Odor Detection Threshold, Neural Net model | bCD Complex Stability Constant |
|---|---|---|---|---|---|
| 104-53-0 | 3-phenyl propionaldehyde | 1.65 | 134.18 | 8.95 | 2.47 |
| 104-54-1 | Cinnamic alcohol | 1.68 | 134.18 | 8.58 | 2.15 |
| 104-55-2 | Cinnamic aldehyde | 1.92 | 132.16 | 8.56 | 2.37 |
| 104-62-1 | Phenethyl formate | 1.82 | 150.18 | 8.10 | 2.32 |
| 104-64-3 | 3-phenyl propyl formate | 2.22 | 164.20 | 8.51 | 2.46 |
| 105-01-1 | Isobutyl furylpropionate | 2.34 | 196.25 | 8.60 | 2.30 |
| 10521-96-7 | Styryl acetate | 2.3 | 162.19 | 8.60 | 1.47 |
| 105-86-2 | geranyl formate | 2.44 | 182.26 | 8.49 | −1.85 |
| 10606-47-0 | 3-Hepten-1-ol | 1.79 | 114.19 | 8.47 | 2.11 |
| 106-22-9 | Citronellol | 2.49 | 156.27 | 8.37 | −0.64 |
| 106-24-1 | trans-Geraniol | 1.95 | 154.25 | 9.36 | −2.13 |
| 106-25-2 | Nerol | 1.95 | 154.25 | 9.36 | −2.13 |
| 106-26-3 | Neral | 2.33 | 152.24 | 8.48 | −1.82 |
| 106-72-9 | melon heptenal (melonal) | 2.09 | 140.23 | 8.09 | −0.64 |
| 107-03-9 | Propyl mercaptan | 1.87 | 76.16 | 9.04 | 0.65 |
| 1073-26-3 | 2-Propionylpyrrole | 1.37 | 123.15 | 8.13 | 1.88 |
| 110458-85-0 | 5,6-Dimethyl-1-(1-methylethenyl)bicyclo[2.2.1]hept-5-ene-2-methanol | 2.36 | 192.30 | 9.46 | 1.27 |
| 1123-85-9 | Hydratopic alcohol | 1.85 | 136.19 | 8.19 | 1.99 |
| 1131-62-0 | 3,4-Dimethoxyacetophenone | 1.7 | 180.20 | 8.15 | 1.63 |
| 116-26-7 | Safranal | 2.4 | 150.22 | 8.54 | 1.30 |
| 118-93-4 | 2-Hydroxyacetophenone | 1.97 | 136.15 | 8.15 | 1.38 |
| 1197-06-4 | cis-carveol | 1.86 | 152.24 | 8.60 | 0.32 |
| 1205-17-0 | ocean propanal (helional) | 1.77 | 192.21 | 8.89 | 2.67 |
| 120-58-1 | Isosafrol | 2.01 | 162.19 | 8.45 | 2.52 |
| 120-72-9 | Indole | 2.34 | 117.15 | 8.20 | 2.19 |
| 120-75-2 | 2-Methylbenzothiazole | 2.14 | 149.21 | 8.12 | 2.83 |
| 121-32-4 | Ethyl vanillin | 1.53 | 166.18 | 10.32 | 2.41 |
| 121-33-5 | Vanillin | 1.04 | 152.15 | 9.93 | 2.36 |
| 121-98-2 | Methyl p-anisate | 1.99 | 166.18 | 8.54 | 2.05 |
| 122-63-4 | Benzyl propionate | 2.24 | 164.20 | 8.29 | 2.01 |
| 122-72-5 | 3-phenyl propyl acetate | 2.48 | 178.23 | 8.70 | 1.73 |
| 122-78-1 | phenyl acetaldehyde | 1.46 | 120.15 | 8.40 | 2.30 |
| 123-08-0 | p-Hydroxybenzaldehyde | 1.29 | 122.12 | 9.34 | 2.28 |
| 123-11-5 | para-anisaldehyde | 1.53 | 136.15 | 7.72 | 2.29 |
| 123-92-2 | Isoamyl acetate | 1.87 | 130.19 | 7.12 | 1.33 |
| 13327-56-5 | Ethyl 3-methylthiopropionate | 1.47 | 148.22 | 8.09 | 1.88 |
| 134-20-3 | Methyl anthranilate | 1.58 | 151.17 | 8.22 | 1.69 |
| 13494-08-1 | 1,2-Cyclopentanedione, 3-ethyl- | 0.5 | 126.16 | 8.29 | 2.72 |
| 134-96-3 | Syringaldehyde | 0.94 | 182.18 | 9.89 | 2.48 |
| 13678-68-7 | furfuryl thioacetate | 1.09 | 156.20 | 8.11 | 1.33 |
| 13679-85-1 | blackberry thiophenone | 0.73 | 116.18 | 8.44 | 2.06 |
| 140-39-6 | p-Cresyl acetate | 2.17 | 150.18 | 8.10 | 1.67 |
| 14049-11-7 | linalool oxide (pyranoid) | 1.89 | 170.25 | 8.45 | 2.62 |
| 141-27-5 | Geranial | 2.33 | 152.24 | 8.48 | −1.82 |
| 142653-61-0 | Parmanyl | 1.75 | 153.22 | 8.13 | 2.05 |
| 142-83-6 | Sorbinaldehyde | 1.29 | 96.13 | 8.57 | 2.29 |
| 14360-50-0 | Pentyl 2-furyl ketone | 2.49 | 166.22 | 9.39 | 2.44 |
| 150-19-6 | m-Guaiacol | 1.39 | 124.14 | 8.16 | 2.02 |
| 1504-55-8 | alpha-Methylcinnamic alcohol (cypriol) | 1.73 | 148.20 | 8.68 | 0.74 |
| 15111-56-5 | Ethyl cyclohex-3-enecarboxylate | 1.86 | 154.21 | 8.47 | 2.78 |
| 1516-17-2 | 2,4-Hexadienyl acetate | 1.75 | 110.16 | 8.30 | 1.36 |
| 15174-69-3 | 4-Hydroxy-3-methylbenzaldehyde | 1.63 | 136.15 | 10.25 | 2.24 |
| 15186-51-3 | Furan, 3-methyl-2-(3-methyl-2-butenyl)- | 2.04 | 150.22 | 8.26 | −0.46 |
| 1540-28-9 | n-Pentyl acetoacetate | 1.63 | 172.22 | 8.04 | 1.79 |
| 1552-67-6 | Ethyl 2-hexenoate | 2.49 | 142.20 | 8.30 | 2.12 |
| 15679-12-6 | 2-Ethyl-4-methylthiazole | 1.69 | 127.20 | 8.31 | 2.13 |
| 15679-13-7 | tropical thiazole | 2.12 | 141.23 | 8.25 | 2.33 |
| 16251-77-7 | Trifernal | 2.28 | 148.20 | 8.87 | 2.51 |
| 1646-26-0 | Coumarone | 1.9 | 160.17 | 8.64 | 1.90 |
| 16491-25-1 | 2,4-Hexadienyl propionate | 2.44 | 154.21 | 8.72 | 1.97 |
| 1679-07-8 | Cyclopentyl mercaptan | 2.24 | 102.19 | 9.09 | 1.47 |
| 1679-09-0 | 2-Methyl-2-butanethiol | 2.45 | 104.21 | 9.16 | 0.79 |
| 16957-70-3 | trans-2-Methyl-2-pentenoic acid (Strawberriff) | 1.33 | 114.14 | 8.78 | 0.65 |
| 1708-34-5 | 2-Hexyl-1,3-dioxolane | 2.17 | 158.24 | 8.11 | 2.56 |
| 1708-81-2 | cis-3-Hepten-1-ol | 1.79 | 114.19 | 8.47 | 2.11 |
| 1708-82-3 | 3-Hexenyl acetate | 2.18 | 142.20 | 8.16 | 1.48 |
| 17102-64-6 | Trans, trans-2,4-Hexadien-1-01 | 0.96 | 98.14 | 8.22 | 2.06 |
| 1754-62-7 | Methyl Trans-Cinnamate, 99% | 2.44 | 162.19 | 8.97 | 2.07 |

TABLE 6-continued

| CAS Number | Name | LogP (v3.0) | Formula Weight | Odor Detection Threshold, Neural Net model | bCD Complex Stability Constant |
|---|---|---|---|---|---|
| 1759-28-0 | 4-Methyl-5-vinylthiazole | 1.51 | 125.19 | 8.56 | 1.62 |
| 17626-75-4 | 2-Propylthiazole | 1.51 | 127.20 | 8.23 | 1.79 |
| 18031-40-8 | (S),(−)-Perillaaldehyde | 2.34 | 150.22 | 9.80 | 1.85 |
| 18277-27-5 | 2-(1-Methylpropyl)thiazole | 1.9 | 141.23 | 8.25 | 1.71 |
| 18479-68-0 | (+)-P-Menth-1-en-9-ol, 97%, mixture of isomers | 2.26 | 154.25 | 8.87 | 1.66 |
| 18640-74-9 | Isobutyl thiazole | 1.92 | 141.23 | 8.29 | 2.02 |
| 18829-55-5 | trans-2-Heptenal | 2.1 | 112.17 | 8.76 | 2.33 |
| 18881-04-4 | (1S)-(−)-cis-Verbenol | 2.03 | 152.24 | 8.09 | 2.61 |
| 189440-77-5 | Anapear | 2.3 | 154.21 | 8.78 | 2.20 |
| 1901-38-8 | alpha-Campholenic alcohol | 2.03 | 154.25 | 8.08 | 1.32 |
| 19788-49-9 | Ethyl 2-mercaptopropionate | 1.41 | 134.19 | 8.39 | 0.99 |
| 19819-98-8 | 2-Methylphenethyl alcohol | 1.66 | 136.19 | 8.46 | 2.36 |
| 2046-17-5 | Methyl 4-phenylbutyrate | 2.46 | 178.23 | 8.75 | 2.37 |
| 20474-93-5 | Allyl crotonate | 1.63 | 126.16 | 8.29 | 2.24 |
| 2051-78-7 | Allyl butyrate | 1.88 | 128.17 | 8.17 | 2.21 |
| 2051-96-9 | Benzyl lactate | 1.35 | 180.20 | 8.15 | 1.70 |
| 20665-85-4 | Vanillin isobutyrate | 1.92 | 222.24 | 8.20 | 2.20 |
| 2111-75-3 | perillaldehyde | 2.34 | 150.22 | 9.80 | 1.85 |
| 2142-94-1 | Neryl Formate | 2.44 | 182.26 | 8.49 | −1.85 |
| 2179-58-0 | Allyl methyl disulfide | 1.9 | 120.23 | 8.59 | 1.44 |
| 2179-60-4 | Methyl propyl disulfide | 2.28 | 122.24 | 8.56 | 1.97 |
| 21835-00-7 | 2-Cyclopenten-1-one, 2-hydroxy-3,4-dimethyl- | −0.02 | 126.16 | 8.91 | 0.76 |
| 21835-01-8 | 3-Ethyl-2-hydroxy-2-cyclopenten-1-one | 0.06 | 126.16 | 8.79 | 2.41 |
| 22104-78-5 | 2-Octenol-1 | 2.27 | 128.21 | 8.81 | 2.24 |
| 2217-33-6 | Tetrahydrofurfuryl butyrate | 1.54 | 172.22 | 8.40 | 2.22 |
| 22451-63-4 | Allo-ocimenol | 2.42 | 152.24 | 8.51 | −0.99 |
| 22460-95-3 | 7-Octene-1,6-diol, 3,7-dimethyl- | 1.33 | 172.27 | 8.27 | 0.79 |
| 22924-15-8 | 3-Ethoxybenzaldehyde | 1.99 | 150.18 | 8.14 | 2.33 |
| 22927-13-5 | 2-Ethylbenzaldehyde | 2.06 | 134.18 | 8.78 | 2.53 |
| 2305-21-7 | 2-hexen-1-ol | 1.3 | 100.16 | 8.09 | 2.06 |
| 23495-12-7 | Phenoxyethyl propionate | 2.43 | 194.23 | 8.92 | 1.78 |
| 23911-56-0 | Nerolione | 2.02 | 174.20 | 8.74 | 2.04 |
| 2445-83-2 | 7-Methylcoumarin | 2.42 | 160.17 | 8.79 | 2.78 |
| 2463-63-0 | Butylacrolein | 2.1 | 112.17 | 8.76 | 2.33 |
| 2497-18-9 | 2-Hexen-1-yl acetate | 2.21 | 142.20 | 8.20 | 1.45 |
| 2555-49-9 | Ethyl phenoxyacetate | 2.04 | 180.20 | 8.36 | 1.93 |
| 26553-46-8 | Ethyl trans-3-hexenoate | 2.25 | 142.20 | 8.34 | 2.14 |
| 8/6/2719 | N-Acetyl methyl anthranilate | 1.21 | 193.20 | 8.00 | 1.48 |
| 27829-72-7 | Ethyl trans-2-hexenoate | 2.49 | 142.20 | 8.30 | 2.12 |
| 27939-60-2 | Vertoliff (triplal extra) | 1.8 | 138.21 | 9.24 | 1.71 |
| 28069-72-9 | (2E,6Z)-Nona-2,6-dien-1-ol | 2.43 | 140.23 | 9.59 | 2.24 |
| 28977-58-4 | Ocimenol | 2.02 | 152.24 | 8.71 | −0.59 |
| 29414-56-0 | 2,6-Dimethyl-1,5,7-octatrienol-3 | 1.96 | 152.24 | 8.89 | −0.76 |
| 29548-14-9 | p-Menth-1-ene-9-al | 2.24 | 152.24 | 9.40 | 1.85 |
| 30361-28-5 | 2,4-Octadien-1-al | 2.45 | 124.18 | 9.33 | 2.32 |
| 30954-98-4 | Propyl anthranilate | 2.47 | 179.22 | 8.88 | 1.87 |
| 3194-17-0 | 2-Pentanoylfuran | 1.99 | 152.19 | 8.97 | 2.40 |
| 32272-48-3 | 4-Ethyl-2-methylthiazole | 1.7 | 127.20 | 8.32 | 2.25 |
| 32764-98-0 | Jasmolactone | 2.36 | 168.24 | 8.72 | 2.96 |
| 33467-73-1 | cis-3-Hexenyl formate | 1.69 | 128.17 | 8.22 | 2.25 |
| 3391-86-4 | 1-Octenol-3 | 2.36 | 128.21 | 8.29 | 2.19 |
| 3581-91-7 | 4,5-Dimethylthiazole | 0.91 | 113.18 | 8.10 | 1.30 |
| 3583-00-4 | 4,4-Dimethyl-5-isopropyl-1,3-dioxolane | 1.92 | 158.24 | 8.99 | 1.98 |
| 35926-04-6 | 1-Hexen-3-yl acetate | 2.31 | 142.20 | 8.02 | 1.68 |
| 36701-01-6 | Furfuryl valerate | 1.89 | 182.22 | 8.39 | 2.12 |
| 36806-46-9 | 2,6-Dimethyl-6-hepten-1-ol | 2.4 | 142.24 | 8.07 | 0.76 |
| 3681-71-8 | cis-3-Hexenyl acetate | 2.18 | 142.20 | 8.16 | 1.48 |
| 3681-82-1 | trans-3-Hexenyl acetate | 2.18 | 142.20 | 8.16 | 1.48 |
| 36880-33-8 | 5-Ethyl-2-thiophenecarbaldehyde | 1.85 | 140.20 | 8.19 | 2.64 |
| 37973-51-6 | 2-Phenyl-1(2)propenyl-1 ester | 2.47 | 176.22 | 8.82 | 0.44 |
| 38142-45-9 | 3-Cyclohexene-1-ethanol, 4-methyl-.beta.-methylene-, €- | 1.84 | 152.24 | 8.62 | 1.58 |
| 39252-02-3 | Furfuryl hexanoate | 2.38 | 196.25 | 8.80 | 2.17 |
| 39677-52-6 | 3-Methoxy Cinnamaldehyde | 1.86 | 162.19 | 8.84 | 2.49 |
| 40010-99-9 | 3-Acetyl-5-butyldihydro-2(3H)-furanone | 1.71 | 184.24 | 8.57 | 2.58 |
| 40790-29-2 | Pyrazine, 3-butyl-2,5-dimethyl- | 2.29 | 164.25 | 8.18 | 2.48 |
| 409-02-9 | Methyl Heptenone | 2.27 | 126.20 | 8.58 | 2.38 |
| 4175-66-0 | 2,5-Dimethylthiazole | 0.94 | 113.18 | 8.08 | 1.63 |
| 4180-23-8 | €-anethol | 2.43 | 148.20 | 8.79 | 2.34 |

TABLE 6-continued

| CAS Number | Name | LogP (v3.0) | Formula Weight | Odor Detection Threshold, Neural Net model | bCD Complex Stability Constant |
|---|---|---|---|---|---|
| 41847-88-5 | Phenylethyl oxy-acetaldehyde | 1.55 | 164.20 | 8.61 | 2.34 |
| 42348-12-9 | 3-Ethyl-2-hydroxy-4-methylcyclopent-2-en-1-one | 0.54 | 140.18 | 9.10 | 2.58 |
| 3/5/4313 | (E,E)-2,4-heptadien-1-al | 1.98 | 110.16 | 9.00 | 2.29 |
| 6/1/4364 | Cinnamic aldehyde dimethyl acetal | 2.02 | 178.23 | 8.44 | 2.03 |
| 4501-58-0 | Campholene aldehyde | 2.2 | 152.24 | 8.31 | 1.43 |
| 4634-89-3 | cis-4-Hexenal | 1.05 | 98.14 | 9.24 | 2.26 |
| 4643-25-8 | 2-Hepten-4-one | 1.85 | 112.17 | 8.31 | 2.21 |
| 4643-27-0 | 2-Octen-4-one | 2.42 | 126.20 | 8.70 | 2.43 |
| 473-67-6 | Verbenol | 2.03 | 152.24 | 8.09 | 2.61 |
| 4748-78-1 | 4-Ethylbenzaldehyde | 2.39 | 134.18 | 9.19 | 2.54 |
| 491-04-3 | Piperitol | 2.4 | 154.25 | 8.70 | 1.72 |
| 491-09-8 | piperitenone | 2.33 | 150.22 | 8.40 | −1.20 |
| 491-31-6 | Isocoumarin | 1.69 | 146.15 | 8.63 | 2.45 |
| 491-35-0 | Lepidine | 2.46 | 143.19 | 8.13 | 2.44 |
| 11/8/4940 | ethyl maltol | 0.17 | 140.14 | 7.44 | 1.94 |
| 496-77-5 | Butyroin | 1.29 | 144.21 | 8.36 | 2.22 |
| 499-44-5 | Hinokitiol | 1.35 | 164.20 | 9.32 | 2.71 |
| 50888-63-6 | Pyrazine, 2-butyl-3,5-dimethyl- | 2.3 | 164.25 | 8.19 | 2.27 |
| 53046-97-2 | cis-3, cis-6-nonadienol | 2.45 | 140.23 | 9.52 | 2.16 |
| 53398-78-0 | trans-2-Hexenyl formate | 1.71 | 128.17 | 8.31 | 2.23 |
| 53399-81-8 | Ethyl 2-methyl-4-pentenoate | 2.26 | 142.20 | 8.16 | 2.08 |
| 536-50-5 | 1-(4-Methylphenyl)ethanol | 2 | 136.19 | 8.07 | 2.39 |
| 536-59-4 | Perillyl alcohol | 1.83 | 152.24 | 8.58 | 1.69 |
| 536-60-7 | Cumic alcohol | 2.39 | 150.22 | 8.68 | 2.39 |
| 5392-40-5 | Citral | 2.33 | 152.24 | 8.48 | −1.82 |
| 5396-89-4 | Benzyl acetoacetate | 1.43 | 192.21 | 8.05 | 1.45 |
| 12/2/5406 | p-Methylhydrocinnamic aldehyde | 2.19 | 148.20 | 9.57 | 2.84 |
| 541-58-2 | 2,4-Dimethylthiazole | 1.24 | 113.18 | 8.08 | 1.89 |
| 5426-78-8 | Acetaldehyde phenyl ethyl acetal | 2.22 | 166.22 | 8.56 | 1.83 |
| 6/6/5462 | Canthoxal | 2.16 | 178.23 | 8.80 | 2.49 |
| 6/8/5466 | Ethyl 3-mercaptopropionate | 1.36 | 134.19 | 8.92 | 1.25 |
| 5471-51-2 | Raspberry ketone | 1.58 | 164.20 | 7.67 | 1.70 |
| 554-14-3 | 2-Methylthiophene | 2.06 | 98.16 | 8.11 | 1.52 |
| 55722-59-3 | 3,6-Octadienal, 3,7-dimethyl- | 2.34 | 152.24 | 8.51 | −1.89 |
| 5577-44-6 | 2,4-Octadienal | 2.45 | 124.18 | 9.33 | 2.32 |
| 5660-60-6 | Cinnamaldehyde ethylene glycol acetal | 2.15 | 176.22 | 8.04 | 2.16 |
| 56805-23-3 | trans-3, cis-6-nonadienol | 2.45 | 140.23 | 9.52 | 2.16 |
| 57266-86-1 | 2-Heptenal, (2Z)- | 2.1 | 112.17 | 8.76 | 2.33 |
| 57500-00-2 | Methyl furfuryl disulfide | 1.92 | 160.25 | 8.19 | 2.38 |
| 579-74-8 | o-Acetylanisole | 1.55 | 150.18 | 8.40 | 1.56 |
| 58461-27-1 | Lavandulol | 1.95 | 154.25 | 8.98 | −1.82 |
| 585-74-0 | 3-Methylacetophenone | 2.27 | 134.18 | 8.23 | 1.65 |
| 589-18-4 | p-Tolyl alcohol | 1.62 | 122.17 | 8.01 | 2.35 |
| 59020-85-8 | Furfuryl thiopropionate | 1.61 | 170.23 | 8.45 | 2.16 |
| 59021-02-2 | 2-Mercaptomethylpyrazine | 0.34 | 126.18 | 8.26 | 0.66 |
| 5910-85-0 | 2,4-Heptadienal | 1.98 | 110.16 | 9.00 | 2.29 |
| 5912-86-7 | cis-iso-Eugenol | 1.85 | 164.20 | 8.60 | 2.38 |
| 5925-68-8 | S-Ethyl benzothioate | 2.21 | 152.21 | 8.74 | 1.83 |
| 5932-68-3 | trans-Isoeugenol | 1.85 | 164.20 | 8.60 | 2.38 |
| 606-27-9 | Methyl 2-nitrobenzoate | 1.57 | 181.15 | 8.45 | 2.25 |
| 606-45-1 | Methyl o-methoxybenzoate | 1.79 | 166.18 | 8.56 | 2.15 |
| 613-70-7 | Guaiacyl acetate | 1.55 | 166.18 | 8.18 | 1.57 |
| 616-44-4 | 3-Methylthiophene | 2.23 | 98.16 | 8.51 | 1.52 |
| 6191-71-5 | cis-4-Hepten-1-ol | 1.77 | 114.19 | 8.46 | 2.11 |
| 6192-44-5 | beta-Phenoxy ethyl acetate | 1.87 | 180.20 | 8.51 | 1.26 |
| 61931-81-5 | cis-3-Hexenyl lactate | 1.34 | 172.22 | 8.20 | 1.76 |
| 620-23-5 | meta-tolyl aldehyde | 2.13 | 120.15 | 8.79 | 2.38 |
| 623-15-4 | 4-(2-Furyl)-3-buten-2-one | 1.7 | 136.15 | 8.42 | 1.38 |
| 624-92-0 | Dimethyl disulfide | 1.06 | 94.19 | 8.64 | 0.27 |
| 6290-14-8 | Cyclopentyl isobutyrate | 2.29 | 156.22 | 8.42 | 2.08 |
| 6314-97-2 | Phenylacetaldehyde diethyl acetal | 2.29 | 194.27 | 9.02 | 2.37 |
| 637-65-0 | tetrahydrofurfuryl propionate | 0.93 | 158.20 | 8.02 | 2.07 |
| 638-02-8 | 2,5-Dimethylthiophene | 2.36 | 112.19 | 8.64 | 2.04 |
| 64988-06-3 | Ethyl 2-methoxybenzyl ether | 1.98 | 166.22 | 8.23 | 2.27 |
| 65405-67-6 | p-Methoxy-alpha-methyl cinnamaldehyde | 2 | 176.22 | 8.85 | 1.16 |
| 65405-73-4 | Geranyl oxyacetaldehyde | 2.32 | 196.29 | 8.71 | −1.88 |
| 67028-40-4 | Ethyl (p-tolyloxy)acetate | 2.49 | 194.23 | 8.45 | 2.18 |
| 6728-26-3 | Trans-2-Hexenal | 1.57 | 98.14 | 8.41 | 2.26 |
| 6728-31-0 | cis-4-Heptenal | 1.85 | 112.17 | 9.51 | 2.33 |
| 67633-97-0 | 3-Mercapto-2-pentanone | 1.37 | 118.19 | 8.86 | 0.23 |

TABLE 6-continued

| CAS Number | Name | LogP (v3.0) | Formula Weight | Odor Detection Threshold, Neural Net model | bCD Complex Stability Constant |
|---|---|---|---|---|---|
| 67634-07-5 | 3,5,6-Trimethyl-3-cyclohexene-1-carbaldehyde | 2.37 | 152.24 | 8.63 | 1.97 |
| 67634-16-6 | Floralol | 1.83 | 140.23 | 8.38 | 1.50 |
| 67634-17-7 | 2,4-Dimethyl-3-cyclohexene-1-methanol | 1.81 | 140.23 | 8.51 | 1.61 |
| 67746-30-9 | trans-2-Hexenal diethyl acetal | 2.34 | 172.27 | 8.19 | 2.13 |
| 67801-65-4 | 3,6-ivy carbaldehyde | 1.8 | 138.21 | 9.25 | 2.09 |
| 67845-46-9 | p-Methyl phenoxy acetaldehyde | 1.76 | 150.18 | 8.64 | 2.40 |
| 6789-80-6 | (Z)-3-hexen-1-al | 1.43 | 98.14 | 8.97 | 2.26 |
| 68039-48-5 | Dimethyl cyclohexene carboxaldehyde | 1.82 | 138.21 | 9.18 | 1.65 |
| 68039-49-6 | 2,4-Dimethyl-3-Cyclohexene-1-carboxaldehyde (Ligustral) | 1.78 | 138.21 | 9.24 | 1.76 |
| 68133-76-6 | cis-3-Hexenyl pyruvate | 1.9 | 170.21 | 8.50 | 1.30 |
| 68737-61-1 | 3,5-ivy carbaldehyde | 1.82 | 137.61 | 9.18 | 1.65 |
| 698-76-0 | delta-Octalactone | 2.03 | 142.20 | 8.24 | 2.83 |
| 699-10-5 | Methyl benzyl disulfide | 2.47 | 170.29 | 8.45 | 2.96 |
| 701-70-2 | 1-Phenylbutan-2-ol | 2.21 | 150.22 | 8.59 | 2.26 |
| 7452-79-1 | Ethyl 2-methylbutyrate | 1.91 | 130.19 | 7.27 | 1.75 |
| 74-93-1 | Methyl mercaptan | 0.58 | 48.10 | 8.63 | 0.43 |
| 7493-63-2 | Allyl anthranilate | 2.31 | 177.20 | 8.48 | 1.95 |
| 7493-71-2 | Allyl tiglate | 1.86 | 140.18 | 8.12 | 0.69 |
| 75-08-1 | Ethanethiol | 1.37 | 62.13 | 8.87 | 0.63 |
| 75-18-3 | dimethyl sulfide | 1.24 | 62.13 | 8.33 | 0.86 |
| 75-33-2 | 2-Propanethiol | 1.65 | 76.16 | 9.26 | 0.87 |
| 7540-51-4 | (−)-Citronellol | 2.49 | 156.27 | 8.37 | 0.64 |
| 7549-33-9 | Anisyl propionate | 2.23 | 194.23 | 8.45 | 2.08 |
| 75-66-1 | tert-Butyl mercaptan | 1.65 | 90.18 | 9.13 | 1.13 |
| 764-40-9 | 2,4-Pentadienal | 0.7 | 82.10 | 8.16 | 2.37 |
| 76649-25-7 | 3,6-Nonadien-1-ol | 2.45 | 140.23 | 9.52 | 2.16 |
| 774-48-1 | Benzaldehyde diethyl acetal | 2.03 | 180.25 | 8.57 | 2.35 |
| 7774-74-5 | 2-Thienyl mercaptan | 1.77 | 116.20 | 8.00 | 0.81 |
| 7774-79-0 | 4-(p-Tolyl)-2-butanone | 2.46 | 162.23 | 8.64 | 2.01 |
| 7774-96-1 | Isoeugenyl formate | 2.35 | 192.21 | 8.84 | 2.71 |
| 7786-44-9 | 2,6-Nonadien-1-ol | 2.43 | 140.23 | 9.59 | 2.24 |
| 7786-61-0 | 2-Methoxy-4-vinylphenol | 2.24 | 150.18 | 8.71 | 2.37 |
| 7786-67-6 | p-Menth-8-en-3-ol (8CI) | 2.48 | 154.25 | 8.42 | 2.29 |
| 81925-81-7 | filbert 22eptanone (Filbertone) | 2.31 | 126.20 | 8.06 | 1.92 |
| 84434-18-4 | Gardamide | 2.16 | 191.27 | 8.08 | 1.98 |
| 85-91-6 | Dimethyl anthranilate | 2.19 | 165.19 | 8.13 | 2.08 |
| 870-23-5 | Allyl mercaptan | 1.42 | 74.14 | 9.00 | 0.85 |
| 87-25-2 | Ethyl anthranilate | 2.05 | 165.19 | 8.58 | 1.84 |
| 874-66-8 | cinnamon acrolein | 1.29 | 136.15 | 8.09 | 0.92 |
| 881-68-5 | Vanillin acetate | 0.95 | 194.19 | 8.11 | 1.94 |
| 89-79-2 | Isopulegol | 2.48 | 154.25 | 8.42 | 2.29 |
| 90-02-8 | Salicylaldehyde | 1.4 | 122.12 | 8.95 | 2.21 |
| 90-05-1 | Guaiacol | 1.33 | 124.14 | 8.06 | 1.98 |
| 90-87-9 | Hydratropaldehyde dimethyl acetal | 2.12 | 180.25 | 8.60 | 2.24 |
| 91-64-5 | Coumarin | 1.68 | 146.15 | 8.55 | 2.47 |
| 928-94-9 | (Z)-2-hexen-1-ol | 1.3 | 100.16 | 8.09 | 2.06 |
| 928-95-0 | €-2-hexen-1-ol | 1.3 | 100.16 | 8.09 | 2.06 |
| 928-96-1 | cis-3-Hexen-1-ol | 1.3 | 100.16 | 8.06 | 2.06 |
| 93-16-3 | Methyl isoeugenol | 2.05 | 178.23 | 8.70 | 2.49 |
| 93-29-8 | Isoeugenyl acetate | 2.17 | 206.24 | 8.38 | 1.94 |
| 93-53-8 | 2-phenyl propionaldehyde | 2.06 | 134.18 | 8.43 | 2.21 |
| 93-54-9 | 1-Phenyl-1-propanol | 1.77 | 136.19 | 8.21 | 2.03 |
| 93-58-3 | Methyl benzoate | 1.86 | 136.15 | 8.03 | 2.00 |
| 93-89-0 | Ethyl benzoate | 2.25 | 150.18 | 8.60 | 2.18 |
| 93893-89-1 | Citronitrile | 2.34 | 171.24 | 8.57 | 1.27 |
| 93-92-5 | Styrallyl acetate | 2.2 | 164.20 | 8.18 | 1.54 |
| 94089-01-7 | Butanoic acid, 2-methyl-, 2-hexenyl ester, €- | 1.6 | 134.24 | 9.32 | 1.41 |
| 94-86-0 | Vanitrope | 2.42 | 178.23 | 8.53 | 2.39 |
| 95-20-5 | 2-Methylindole | 2.43 | 131.18 | 8.53 | 2.58 |
| 97-53-0 | Eugenol | 2.21 | 164.20 | 8.57 | 2.51 |

One grouping of perfume raw materials that have a complex stability constant of about 3.0 or less, a ClogP of about 2.5 or less, and a weight average molecular weight of about 200 Daltons or less includes beta gamma hexanol; cis 3 hexenyl acetate; ethyl-2-methyl butyrate; amyl-acetate (isomer blends); vanillin; anethole; methyl isoeugenol; guiacol; floralol; ethyl vanillin; 2,6-nonadien-1-ol; coumarin; and combinations thereof.

Another group of perfume raw materials that have a complex stability constant of about 3.0 or less, a ClogP of about 2.5 or less, and a weight average molecular weight of about 200 Daltons or less includes ethyl-2-methyl butyrate; beta gamma hexanol; iso amyl acetate; amyl acetate; cis-3-Hexenyl acetate; gamma-Octalactone; ethyl vanillin; vanillin; benzaldehyde; and combinations thereof. An additional group of perfume raw materials that have a complex stability constant of about 3.0 or less, a ClogP of about 2.5 or less, and a weight average molecular weight of about 200 Daltons or less includes dimethyl anthranilate; iso-eugenyl acetate; canthoxal; 3,6-nonadien-1-ol, triplal; and combinations thereof. Ethyl-2-methyl butyrate, Beta gamma hexenol, Iso amyl acetate, Amyl acetate, cis-3-Hexenyl Acetate, gamma-Octalactone, Ethyl Vanillin, Vanillin, Benzaldehyde.

Some examples of perfume raw materials with an odor detection threshold of 7-log ppb or more include can be found in the chart above.

Perfumes may be present in the odor control compositions of the present disclosure in an amount of about 3 percent by weight or greater or more preferably about 4 percent by weight or greater, specifically reciting all values within these ranges and any ranges created thereby. For example, perfumes may be present in an amount of about 3 percent by weight to about 6 percent by weight or more preferably from about 4 percent by weight to about 6 percent by weight, specifically including all values within these ranges and any ranges created thereby.

Without wishing to be bound by theory, it is believed that below about 4 percent by weight of perfume may not provide the desired level of odor control in the article during use. It is also believed that above about 6 percent by weight, the perfume described herein may not be completely encapsulated by the substituted cyclodextrin. For example, where it is desired to create a very low perfume bloom or no perfume bloom for the user upon initial removal of the absorbent article from its packaging, perfume levels at or below about 6 weight percent may be beneficial. With the weight percentages of substituted cyclodextrin disclosed herein, perfume levels at or below about 6 percent are believed to be able to be substantially, if not completely, encapsulated by the substituted cyclodextrin.

However, where it is desired to provide the user with an initial perfume bloom prior to use of the absorbent article and an additional bloom upon activation (wetting) of the substituted cyclodextrin, then perfume levels above about 6 percent by weight may be utilized. It is believed that weight percentage levels of greater than about 10.4 percent by weight may be too overpowering as roughly 40 percent of the perfume in the aqueous odor control composition could be un-encapsulated. Above about 40 percent of un-encapsulated perfume is believed to create an overpowering initial scent bloom in the disposable absorbent article.

Position-Specific-Substituted-Cyclodextrins

The odor control compositions of the present disclosure comprise cyclodextrin complexes that are position-specific-substituted cyclodextrins comprising one or more odor controlling compounds, hereafter, "substituted cyclodextrin complexes." The position-specific-substituted cyclodextrins described herein comprises various degrees of substitution in the 2, 3, and 6 positions. As discussed herein, position-specific-substituted cyclodextrins with substitution in positions 2 and 6 provide benefits over conventional β-cyclodextrins and over completely substituted cyclodextrins, i.e. complete substitution in positions, 2, 3, and 6. There are many benefits to utilizing position-specific-substituted cyclodextrins. For example, position-specific-substituted cyclodextrins have a higher solubility than their conventional β-cyclodextrin counterparts. The increased solubility can provide more rapid release of encapsulated fragrances in the position-specific-substituted cyclodextrin. Also, with the increased solubility, less moisture may be required to liberate encapsulated fragrances in the position-specific-substituted cyclodextrin. This increased solubility can also mean that less position-specific-substituted cyclodextrin may be utilized in absorbent articles than their β-cyclodextrin counterparts.

Because of the increased solubility of the position-specific-substituted cyclodextrins, there are methods of application of the position-specific-substituted cyclodextrins which are not available for their conventional β-cyclodextrin counterparts. With the new methods of application, the position-specific-substituted cyclodextrins may be provided to areas of the absorbent article which may not have been possible with their conventional β-cyclodextrin counterparts. Additionally, the position-specific-substituted cyclodextrins can provide higher efficacy than their conventional β-cyclodextrin counterparts.

As known, cyclodextrins are a family of compounds where a number of glucose units are bound together in a ring shaped structure (cyclic oligosaccharides). More specifically cyclodextrins are formed by 5 or more α-D-glucopyranoside units connected through the glycosidic linkages in positions 1 and 4 on the glucose ring. Typically, the number of glucose units forming each ring is from 6 to 12 and the most common forms are those with 6, 7 or 8 glucose units also called alpha-cyclodextrin, beta-cyclodextrin, gamma-cyclodextrin respectively.

In all cyclodextrins, each glucose units have three OH groups bound to the carbon atoms in positions 2, 3 and 6. As mentioned previously, the inventors have surprisingly found that the utilization of position-specific-substituted cyclodextrins provides benefits over their β-cyclodextrin and completely substituted counterparts.

As used herein, the term "position-specific-substituted cyclodextrin" includes any cyclodextrin wherein one or more hydrogen atom of the OH groups in positions 2 and 6 of the glucose units is replaced by a substituent —R thus forming an —OR group. Similarly, as used herein, the term "completely substituted cyclodextrin" includes any cyclodextrin wherein each of the OH groups in positions 2, 3, and 6 have been replaced by OR groups. The average number of —R substituents for each glucose unit in a given sample represents the "degree of substitution" (DS) which is a number ranging from 0 to 3 where 0 corresponds to no substitutions (all OH groups in position 2, 3 and 6 are present) and 3 to a complete substitution (all OH groups in position 2, 3 and 6 are replaced by OR groups). The average is calculated on a molar basis.

The absorbent articles of the present invention comprise substituted cyclodextrin complexes of one or more odor controlling organic compound, wherein the substituted cyclodextrin complex comprises position-specific-substituted cyclodextrins. The substituted cyclodextrin complex has a substitution degree (DS) of 0.4 or more —R substituents per molecule of cyclodextrin and wherein substitution in position 2 is 20% or above, in position 6 is 20% or above.

In some forms of the invention, the average degree of substitution can be between 0.4 and 2.5, between 0.9 and 2.4, between 1.2 and 2.2, between 1.6 and 2.1, specifically reciting all values within these ranges and any ranges created thereby. In some forms of the invention, the substitution in position 2 can be between 20 and 90%, more preferably between 45% and 80%. In some forms of the invention, the substitution in position 6 can be between 20 and 90%, more preferably between 45% and 80%. In some forms, the invention may encompass combinations of the preferred aspects mentioned above.

It is worth noting that position-specific-substituted cyclodextrins are synthesized from conventional cyclodextrins. Via this synthesis, a variety of cyclodextrin molecules are created. For example, some of the cyclodextrin molecules may not be substituted at all, i.e. all OH groups in positions 2, 3, and 6 are present. As another example, some of the cyclodextrin molecules will be substituted as desired, i.e. position-specific-substituted cyclodextrins. And, as another example, some of the cyclodextrins will experience complete substitution, i.e. all OH groups are substituted in positions 2, 3, and 6 by OR groups. However, as discussed herein, the position-specific-substituted cyclodextrins, with substitution in positions 2 and 6, provides additional benefits over the completely substituted cyclodextrins. As such, forms of the present invention are contemplated where the degree of substitution in position 3 is less than the level of substitution in position 2 and/or position 6. In some forms, the degree of substitution in position 3 is less than about 50 percent, less than about 40 percent, less than about 30 percent, less than about 20 percent, or less than about 10 percent, specifically reciting all values within these ranges and any ranges created thereby.

The —R substituents in the —OR groups can be selected from any substituent having a carbon atom in position 1 (thus forming an —O—C— bond with the oxygen atom). Suitable —R substituents may include carbon atoms chains which are saturated or unsaturated and can be straight or branched. For example, suitable —R substituents include saturated and straight chain C1-6 alkyl, hydroxyalkyl, and mixtures thereof. Particularly suitable —R substituents have a carbon chain of from 1 to 6 carbon atoms and are selected from alkyl, hydroxyalkyl, dihydroxyalkyl, carboxy-alkyl, aryl, maltosyl, allyl, benzyl, alkanoyl, and mixtures thereof, wherein the term "alkyl" encompasses both linear and branched alkyl chains.

In some forms, an —R substituent may comprise propyl, ethyl, methyl, and hydroxypropyl. Different —R substituents can be present in the same position-specific-substituted cyclodextrin sample on the same cyclodextrin molecule and even on the same cyclodextrin glucose unit.

In one particular form, all the —R substituents may be methyl substituents. In this case, the cyclodextrin is also called "methylated β-cyclodextrin". For example, a particularly suitable cyclodextrin material for the present invention is a methylated cyclodextrin having a DS of 0.4 or higher, preferably from 0.4 to 2.5, more preferably between 0.9 and 2, even more preferably between 1.2 and 1.8 and wherein at least 20%, preferably between 20% and 90%, more preferably between 45% and 80% of the —OH groups in positions 2 and 6, respectively, are methylated.

The degree of substitution can be measured with gas chromatography as described below, with reference to methyl substituents in β-Cyclodextrin.

It has been surprisingly found that substituted cyclodextrin complexes, according to the present invention, release more rapidly the odor controlling organic compound when the absorbent article is contacted with an aqueous fluid, compared with similar complexes wherein the cyclodextrin does not comprise position-specific-substituted cyclodextrins or where the substitution is distributed between positions 2, 3 and 6.

In general, cyclodextrin complexes, including substituted cyclodextrin complexes, can help prevent the evaporation of the complexed fragrance compounds. In use, moisture from urine or menses contacts the cyclodextrin complex and dissolves the crystalline structure of the cyclodextrin complex. This causes the release of the fragrance materials within the cyclodextrin complex. However, a problem exists when incorporating a cyclodextrin complex in an absorbent hygienic article. Other components, such as the absorbent core and/or superabsorbent material, of the absorbent article have a strong affinity for bodily fluids, e.g. menses and urine, including the moisture contained therein. So, when an absorbent article is insulted with bodily fluid, such as menses or urine, the cyclodextrin complex can be in competition with the absorbent core and/or superabsorbent material for the moisture contained in the bodily fluid. The absorbent core and/or superabsorbent material has a strong affinity for the moisture and once the absorbent core and/or superabsorbent material contacts the bodily fluid, the absorbent core and/or superabsorbent material effectively "lock-up" the moisture of the bodily fluid, thereby reducing the amount of moisture available to contact the cyclodextrin complex. So, only a limited amount of moisture may be available to dissolve the cyclodextrin crystalline structure and release the fragrance compounds to provide odor control benefits.

With conventional cyclodextrin complexes, a larger amount of moisture may be required to solubilize the cyclodextrin molecules and release the encapsulated fragrance. The same holds true for completely substituted cyclodextrins where positions 2, 3, and 6 are substituted. However, the inventors have surprisingly found that with the use of a position-specific-substituted cyclodextrins, as described herein, less moisture may be required to solubilize the position-specific-substituted cyclodextrins. So, more of the complexed fragrance compounds may be released without compromising the absorbent or retention capacity of the absorbent article.

The substituted cyclodextrin may be present in the odor control composition of the present disclosure in an amount of about 40 percent or greater or more preferably about 50 percent or greater, specifically reciting all values within these ranges and any ranges created thereby. For example, the substituted cyclodextrin may be present in the odor control composition of the present disclosure in an amount of from about 40 percent to about 60 percent by weight or more preferably about 50 percent to about 60 percent by weight, specifically reciting all values within this range and any range created thereby. Without wishing to be bound by theory, it is believed that at levels above about 60 percent by weight, the solubility of the substituted cyclodextrin may become problematic.

Determination of Methyl Substituent Distribution

The Methyl Substituent Distribution in Methylated β-Cyclodextrin (hereafter "mBCD") is measured using gas chromatograph with split/splitless injection and flame ionization detection (a suitable instrument is the Agilent 7890B GC available from Agilent, Santa Clara, CA, or equivalent). The β-cyclodextrin is hydrolyzed, reduced and then acetylated for analysis. Additionally, gas chromatography/mass spectrometry (a suitable unit is the 5777A Mass Selective Detector (MSD) also available from Agilent, or equivalent) can be used to identify the acetylated products to confirm peak identity. Both instruments are calibrated and operated as per the manufacturer's instructions.

Derivatization reagents must be used with a purity of greater than or equal to 99%, except for the borohydride (98%), and can be obtained from Sigma Aldrich, or equivalent. Fifty mg of mBCD and 5 mL of 2 M trifluoroacetic acid solution were added to a 50 mL round bottom flask with magnetic stir bar. The reaction vessel was fitted with a water cooled condenser and heated to reflux for 4 hours while stirring. After complete hydrolysis, the reaction mixture was evaporated under vacuum to dryness. Next, the hydrolysis product, 10 mL of ammonium hydroxide (32% in water), and 101 mg sodium borohydride (2.67 mmols) were stirred in a 50 mL round bottom flask at 40° C. for 2 hours. Residual sodium borohydride was quenched via dropwise addition of glacial acetic acid until the solution pH was in the range of 4.5 to 6. The resulting boric acid was removed via sequential additions of methanol (4×20 mL) to the reaction mixture, followed by evaporation under vacuum at 40° C. The reaction product, 10 mL of pyridine, 36 mg of 4-dimethylaminopyridine (0.2947 mmols), and 630 µL acetic anhydride (630 µL, 6.6794 mmols) were added to a 50 mL round bottom flask with magnetic stir bar. The reaction was stirred vigorously at room temperature for 20 hours. The acetylated alditol products were extracted with 10 mL chloroform using a 60 mL separatory funnel and washed three times with 10 mL of deionized water. The chloroform extract was diluted (1:3) with chloroform, and sampled for gas chromatography analysis.

The GC analysis was performed on a 30 m long by 0.250 mm inner diameter column with 5% phenyl arylene methylpolysiloxane phase at a 1 µm film thickness (a suitable column is the DB5MS available from Agilent, or equivalent USP G27 phase). The GC inlet was set at 280° C. in Split mode (5:1 split, glass wool packed liner) with a 3 mL septum purge. A 1.5 mL/minute column flow of helium was set at an oven temperature of 150° C. under constant flow conditions. The detector was set at 300° C. with flows set to the instrument manufacturer's recommended conditions. The GC oven was programmed to begin at 150° C. for 1 min, then ramp at 15° C./min to 250° C., hold for 4 min at 250° C., then ramp at 10° C./min to 315° C. and a final hold of 1 min. 1 µL of the chloroform extract is injected for analysis. It is understood that one skilled in the art can slightly modify the chromatographic conditions to achieve the necessary separation as needed.

GC-MS analysis is performed under the same chromatographic conditions as for the flame ionization detection (FID). The temperature for the MSD transfer line and detector were set to 280° C. and 300° C. respectively. The MSD was configured for electron ionization at −70 eV scanning from 35 m/z to 400 m/z with a scan rate of 257 msec/scan. The Total Ion Chromatogram was evaluated using the fragmentation data in Table 1 to assign retention order of the glucitol products. The retention order was then applied to the GC-FID chromatograms.

For quantification, each peak measured by GC-FID that is associated with a glucitol monomer is integrated to give a peak area. The areas are then used in Equations 1 and 2 to calculate the mole percent (mol %) of each glucitol monomer and reported to the nearest 0.1 mol %. The results from the example chromatogram are given in Table 7.

$$\text{mols glucitol } A = \text{mg } \beta \text{ cyclodextrin} \times \frac{\text{FID area counts for glucitol } A}{\sum \text{FID area counts of all glucitol monomers}} \times \frac{1}{\text{MW}_A} \quad \text{Eq. 1}$$

where $MW_A$ is the molecular weight of the acetylated glucitol and mg β-cyclodextrin is the starting mass of underivatized mBCD.

$$\text{mol \% glucitol } A = \frac{\text{mols glucitol } A}{\sum \text{mols of all glucitol monomers}} \times 100\% \quad \text{Eq. 2}$$

Additionally, the mol % of particular substitutions are calculated by addition of the individual mol %. For example, mol % of all glucitols methylated at the 6 position (denoted in Table 7 as X6) would be the sum of the mol % of S2,6, S3,6 and S2,3,6.

The average degree of substitution was calculated according to Equation 3. Mol % for all glucitol monomers sharing the same number of methyl substituents (0, 1, 2, or, 3) were summed, multiplied by their respective methyl substituent number (0, 1, 2, or 3) and divided by 100. The result is reported to the nearest 0.1 mol %.

$$DS \text{ per glucose unit} = \frac{1}{100} \sum_{i=0}^{3} i \cdot \text{mol \% } x \quad \text{Eq. 3}$$

Where mol % x is equal to the summation of glucitol monomers having same number of methyl groups.

Data from a gas chromatogram of acetylated D-glucitol derivatives prepared from mBCD using the procedure described above is provided in Table 7. Table 7 shows Selected Fragments of Ionized D-Glucitol Acetates while FIG. 1 is an FID trace.

TABLE 7

| | X = Fragment present in mass spectra | | | | | | | | | | | | | | | |
|---|---|---|---|---|---|---|---|---|---|---|---|---|---|---|---|---|
| | m/z | | | | | | | | | | | | | | | |
| Compound | 99 | 113 | 117 | 129 | 145 | 157 | 159 | 161 | 189 | 217 | 231 | 233 | 261 | 289 | 305 | 333 |
| 2,3,6-Tri-O-methyl-D-glucitol, 1,4,5-triacetate | X | X | X | X | | | | X | | | X | | | | | |
| 2,6-Di-O-methyl-D-glucitol, 1,3,4,5-tetraacetate | | | X | X | | | X | | | | X | | | X | | |
| 3,6-Di-O-methyl-D-glucitol, 1,2,4,5-tetraacetate | X | X | | X | | X | X | | X | | X | | | | | |
| 2,3-Di-O-methyl-D-glucitol, 1,4,5,6-tetraacetate | X | | X | | | | X | X | | | X | | X | X | | |
| 6-O-methyl-D-glucitol, 1,2,3,4,5-pentaacetate | X | | | X | X | X | X | | | X | X | | | X | | X |
| 2-O-methyl-D-glucitol, 1,3,4,5,6-pentaacetate | | | X | X | | X | X | | | | X | | | | | X |
| 3-O-methyl-D-glucitol, 1,2,4,5,6-pentaacetate | X | | | X | X | | X | | X | X | X | | X | | | |
| D-glucitol hexaacetate | | | | | X | X | | | | X | | | | X | | |

Table 8 provides data of the substituent distribution for mBCD, the average degree of methylation of the O6 and O2 positions, and the average degree of substitution (DS) per glucose unit.

TABLE 8

| Substituent Distribution | mol % |
|---|---|
| Unsubstituted | 9.1 |
| S2 | 21.9 |
| S3 | 5.8 |
| S6 | 10.4 |
| S2, 3 | 13.7 |
| S2, 6 | 20.1 |
| S3, 6 | 6.1 |
| S2, 3, 6 | 12.8 |
| X6 | 49.5 |
| X2 | 68.6 |
| X3 | 38.5 |
| Avg. DS per Glusose Unit: | 1.6 |

The position-specific-substituted cyclodextrins of the present invention can be prepared by using methods known in the art for the selective modifications of cyclodextrins. For example, by using methods described by Khan et al. (Chem. Rev. 1998, 98, 1977-1996). Alternative synthesis routes for the preparation of the position-specific-substituted cyclodextrins of the invention are known to the chemists skilled in the field and broadly described in literature. For example, U.S. Pat. No. 5,710,268 and the textbooks "Advances in cyclodextrin chemistry" by Werz, Vidal, Guiou, Sollogoub, Matthieu, Wiley-VCH Verlag GmbH ed. 2014; and "Modern Synthetic Methods in Carbohydrate Chemistry: From Monosaccharides to Complex Glycoconjugates", Werz, Daniel B.; Vidal, Sebastian, eds, 2014 Wiley-VHC Verlag GmbH provide additional details.

Once the position-specific-substituted cyclodextrins is provided, substituted cyclodextrin complexes of odor controlling organic compounds which are active against malodors can be prepared as known in the art for the known cyclodextrin complexes, for example using the kneading method described in U.S. Pat. Nos. 5,571,782 and 5,543,157 or, using the spray drying method described in WO2008/104690A2.

An exemplary odor control composition was created in accordance with the present disclosure. The contents and weight percentages are provided below in Table 1.

TABLE 1

| Material | % Liquid Formula 1 |
|---|---|
| mBCD | 50 |
| SPMB 2 (perfume) | 5.2 |
| Surfactant (silicone) | 0.5 |
| Preservative | 0.8 |
| Water (solvent) | 43.5 |

Additionally, while the weight percentages for the components of the odor control composition have been provided heretofore, those weight percentages were provided in the aqueous form. Once the odor control composition is dried, the weight percentages of the components of the odor control composition of the present disclosure, sans water, are provided in Table 2.

TABLE 2

| Material | % solid (solvent evaporated- |
|---|---|
| mBCD | 88.5 |
| SPMB 2 (perfume) | 9.2 |
| Surfactant (silicone) | 0.9 |
| Preservative | 1.4 |
| Water (solvent) | — |

In the dried form, the odor control composition of the present disclosure may comprise substituted cyclodextrin at a weight percentage of from about 80 percent to about 90 percent or more preferably from about 85 percent to about 90 percent, specifically reciting all values within the ranges and any ranges created thereby. The perfume may be present in an amount of from about 8 percent to about 10 percent or more preferably from about 9 percent to about 10 percent, specifically reciting all values within these ranges and any ranges created thereby. The surfactant may be present in an amount of from about 0.3 percent to about 2.0 percent, more preferably from about 0.5 percent to about 2.0 percent or most preferably from about 0.8 percent to about 2.0 percent, specifically reciting all values within these ranges and any ranges created thereby. And, the preservative may be present in an amount of from 0.5 percent to 2.0 percent, more preferably from about 0.8 percent to about 2.0 percent or most preferably from about 1.2 percent to about 2.0 percent, specifically including all values within these ranges and any ranges created thereby.

Absorbent Articles

The odor control compositions of the present disclosure may be provided to an absorbent article in any suitable location or locations. For example, absorbent articles of the present disclosure comprise a topsheet, a backsheet, and an absorbent core disposed between the topsheet and the backsheet. The odor control composition may be provided on the topsheet, on the absorbent core, and/or on an inner surface of the backsheet. When the odor control compositions in the absorbent article is wetted by liquid insult, the substituted cyclodextrin releases the perfume therein to help mask any odors of the liquid insult. So, the odor control composition can be placed in the article where it has access to liquid insults to the absorbent article.

Regarding the specific components of the absorbent article, the topsheet is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), polymeric materials such as apertured formed thermoplastic films, apertured plastic films, and hydroformed thermoplastic films, porous foams, reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

In some forms, the topsheet may be a laminate of two or more materials, e.g. including a nonwoven and a film. In such forms, the nonwoven may form a body-facing surface of the topsheet. Or, the film may form at least a portion of the body-facing surface of the topsheet. Films for use as topsheets are discussed in U.S. Pat. Nos. 4,629,643; 5,460, 623; and. 6,563,013. Additional examples of formed films suitable for use as a topsheet or a portion thereof are described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986.

Nonlimiting examples of woven and nonwoven materials suitable for use as the topsheet or a portion thereof include fibrous materials made from natural fibers, modified natural fibers, synthetic fibers, or combinations thereof. These fibrous materials can be either hydrophilic or hydrophobic, but it is preferable that the topsheet be hydrophobic or rendered hydrophobic. Some suitable nonwoven materials suitable for use as a topsheet are described in U.S. Pat. Nos. 5,792,404 and 5,665,452.

The backsheet can be impervious to liquids (e.g., menses and/or urine) and can be preferably manufactured from a thin plastic film, although other flexible materials may also be used such as nonwovens. As used herein, the term "flexible" refers to materials which are compliant and will readily conform to the general shape and contours of the human body. The backsheet can prevent the exudates absorbed and contained in the absorbent core from wetting articles which contact the absorbent article such as bedsheets, pants, pajamas and undergarments. The backsheet can also be vapor permeable ("breathable"), while remaining fluid impermeable. The backsheet may comprise a woven or nonwoven material, polymeric films such as thermoplastic films of polyethylene or polypropylene, or composite materials such as a film-coated nonwoven material.

The backsheet can comprise panty fastening means applied on its surface, particularly the surface facing outside the absorbent article in order to allow the article to stay in place when worn between the user's crotch and panties. Such panty fastening means can be for example a layer of adhesive or mechanical means such as Velcro® or combination thereof. When an adhesive is present, typically a release paper is also present in order to protect the adhesive before use.

The backsheet and the topsheet can be positioned respectively adjacent the garment surface and the body surface of the absorbent core. The absorbent core can be joined with the topsheet, the backsheet, or both in any manner as is known by attachment means, such as those well known in the art. Embodiments of the present invention are envisioned wherein portions of the entire absorbent core are unattached to either the topsheet, the backsheet, or both.

The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers. Other suitable absorbent core materials include absorbent foams such as polyurethane foams or high internal phase emulsion ("HIPE") foams. Suitable HIPE foams are disclosed in U.S. Pat. Nos. 5,550,167, 5,387,207, 5,352,711, and 5,331,015.

Other suitable materials for use in absorbent cores comprise open celled foams or pieces thereof. The use of foams in absorbent cores is described in additional detail in U.S. Pat. Nos. 6,410,820; 6,107,356; 6,204,298; 6,207,724; 6,444, 716; 8,211,078, and 8,702,668.

In some forms, the absorbent core structure may comprise a heterogeneous mass layer or may utilize methods or parameters such as those described in U.S. patent application Ser. No. 14/715,984, filed May 19, 2015; U.S. patent application Ser. No. 14/750,399, Jun. 25, 2015; U.S. patent application Ser. No. 14/751,969 filed Jun. 26, 2015; U.S. patent application Ser. No. 15/078,132 filed Mar. 23, 2016; U.S. patent application Ser. No. 14/750,596 filed Jun. 25, 2015; U.S. patent application Ser. No. 15/084,902 filed Mar. 30, 2016; U.S. patent application Ser. No. 15/343,989 filed Nov. 4, 2016; U.S. patent application Ser. No. 15/344,273 filed Nov. 4, 2016; U.S. patent application Ser. No. 15/344, 294 filed Nov. 4, 2016; U.S. patent application Ser. No. 14/704,110 filed May 5, 2015; U.S. patent application Ser. No. 15/194,894 filed Jun. 28, 2016; U.S. patent application Ser. No. 15/344,050 filed Nov. 4, 2016; U.S. patent application Ser. No. 15/344,117 filed Nov. 4, 2016; U.S. patent application Ser. No. 15/344,177 filed Nov. 4, 2016; U.S. patent application Ser. No. 15/344,198 filed Nov. 4, 2016; U.S. patent application Ser. No. 15/344,221 filed Nov. 4, 2016; U.S. patent application Ser. No. 15/344,239 filed Nov. 4, 2016; U.S. patent application Ser. No. 15/344,255 filed Nov. 4, 2016; U.S. patent application Ser. No. 15/464,733 filed Nov. 4, 2016; U.S. Provisional Patent Application No. 62/437,208 filed Dec. 21, 2016; U.S. Provisional Patent Application No. 62/437,225 filed Dec. 21, 2016; U.S. Provisional Patent Application No. 62/437,241 filed Dec. 21, 2016; or U.S. Provisional Patent Application No. 62/437, 259 filed Dec. 21, 2016. The heterogeneous mass layer has a depth, a width, and a height.

In some forms, a combination of absorbent core materials may be utilized. For example, forms are contemplated where a first layer of an absorbent core comprises a foam material or pieces thereof as described previously, and a second layer of an absorbent core comprises an airlaid material. Such combinations are described in U.S. Patent Publication No. 2014/0336606 and U.S. Pat. No. 9,649,228.

For some absorbent articles, the absorbent core can be relatively thin, less than about 5 mm in thickness, or less than about 3 mm, or less than about 1 mm in thickness. Thickness can be determined by measuring the thickness at the midpoint along the longitudinal centerline of the pad by any means known in the art while under a uniform pressure of 1.72 kPa.

The absorbent core can comprise superabsorbent materials such as absorbent gelling materials (AGM), including AGM fibers, as is known in the art. The absorbent core can therefore constitute a layer comprising superabsorbent material.

The absorbent article can comprise other additional components, for example between the topsheet and absorbent core, such as a secondary topsheet or acquisition layer. The secondary topsheet or acquisition layer can comprise a tissue layer or a nonwoven, such as carded resin-bonded nonwovens, embossed carded resin-bonded nonwovens, high-loft carded resin-bonded nonwovens, carded through-air bonded nonwovens, carded thermo-bonded nonwovens, spun-bonded nonwovens, and the like. A variety of fibers can be used in the secondary topsheet or acquisition layer, including natural fibers, e.g. wood pulp, cotton, wool, and the like, as well as biodegradeable fibers, such as polylactic acid fibers, and synthetic fibers such as polyolefins (e.g., polyethylene and polypropylene), polyesters, polyamides, synthetic cellulosics (e.g., RAYON®, Lyocell), cellulose acetate, bicomponent fibers, and blends thereof. The basis weight of the secondary topsheet or acquisition layer can vary depending upon the desired application. In some forms, the secondary topsheet or acquisition layer may comprise a super absorbent polymer, e.g. AGM deposited thereon. In such forms, the secondary topsheet or acquisition layer may comprise a first AGM while the absorbent core comprises a second AGM. In some forms, the first AGM may be different than the second AGM.

The absorbent article can comprise further components such as side cuffs, typically found in diapers, or side wings or side flaps, typically found in sanitary napkins.

Absorbent catamenial tampons are absorbent articles for internal use in the vagina which are typically made by a pledget comprising absorbent fibers compressed to a cylindrical shape. Tampons can be "digital tampons" when they have a self-sustaining shape and can be inserted with a finger or "applicator tampons" i.e. tampons which are introduced using an applicator. Tampons can also comprise an extraction cord so to facilitate extraction from the vagina.

Absorbent hygienic articles herein are often commercialized in packages containing a plurality of units, often the package is a plastic film or a carton box. Single units contained within the commercial package can be individually packaged or not.

In some forms, the absorbent articles of the present disclosure may comprise additional layers disposed between the topsheet and the absorbent core and/or between the absorbent core and the backsheet. Some examples include a secondary topsheet, acquisition layer, and/or distribution layer which can be disclosed between the topsheet and the absorbent core. Other examples include distribution layers or liquid-impermeable layers which are disposed between the absorbent core and the backsheet.

Figure 2:
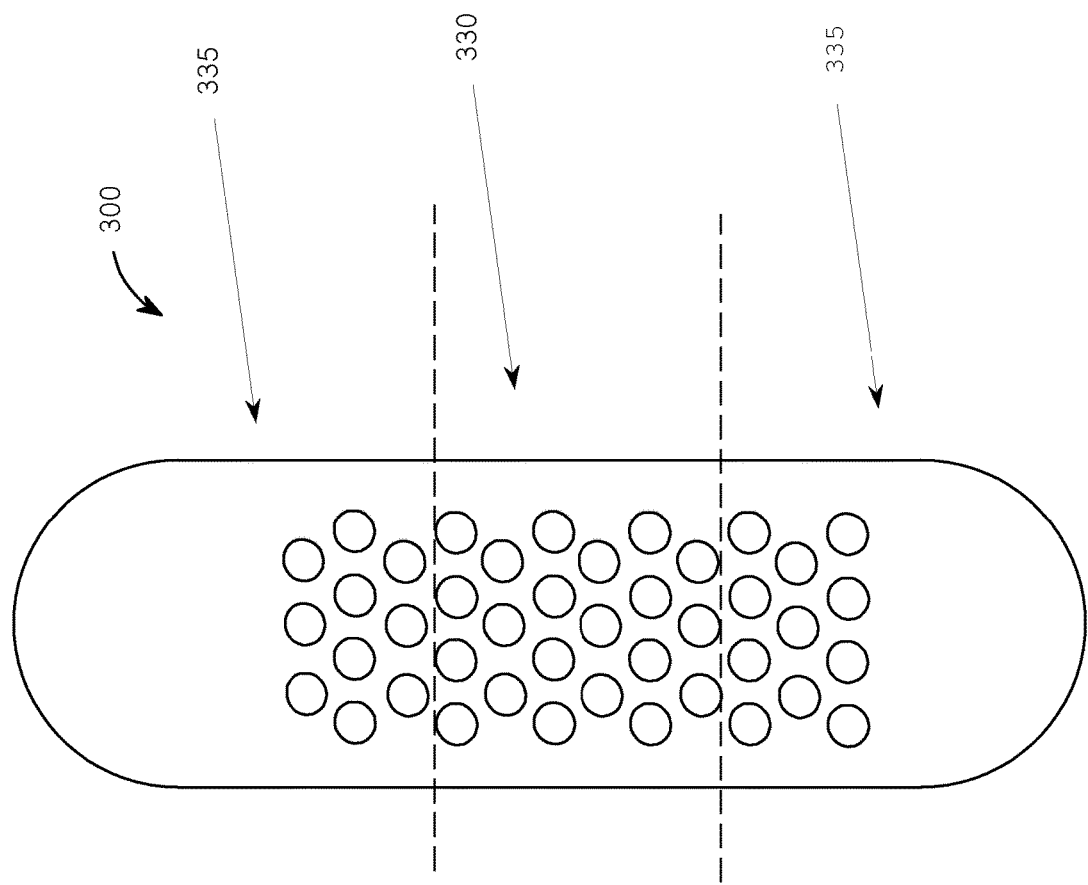
FIG. 2 is a schematic illustration of an absorbent article.

In some forms, the substituted cyclodextrin complex, e.g. mBCD, may be provided in a target zone of an absorbent article. As shown in FIG. 2, the target zone 330 of an absorbent article 300 represents the area of the absorbent article of expected fluid insult. The absorbent article 300 is shown having an overall longitudinal length generally parallel to a Y-axis and an overall lateral width generally parallel to an X-axis. The absorbent article 300 further comprises a thickness in a Z-direction (not shown) which is perpendicular to an X-Y plane created by the X and Y axes.

As shown, the target zone 330 may be disposed between two outer zones 335. In some forms, the target zone 330 may comprise about 60 percent of the overall longitudinal length (along a Y-axis) of the absorbent article 300 where each of the outer zones comprise about 30 percent or less of the overall length or less of the absorbent article 300. In some forms, the target zone 330 may comprise about 50 percent of the overall length while the outer zones 335 comprise about 40 percent or less of the overall length of the absorbent article. In some forms, the target zone 330 may extend from about more than 20 percent to less than about 80 percent, more than about 30 percent to less than about 70 percent, more than about 40 percent to less than about 60 percent of the overall length of the absorbent article 300, specifically including all values within these ranges and any ranges created thereby.

Forms are contemplated where the target zone 300 extends along only a portion of the overall lateral width (along an X-axis) of the absorbent article 300. For example, in some forms, the target zone 330 may extend for less than about 90 percent of the overall width of the absorbent article 300. As another example, the target zone 330 may extend for less than about 75 percent of the overall width of the absorbent article 300. Still in other forms, the target zone 330 may extend for less than about 50 percent of the overall width of the absorbent article 300. As yet another example, the target zone 330 may extend for about more than 10 percent to less than about 90 percent, more than about 20 percent to less than about 80 percent, more than about 30 percent to less than about 70 percent of the overall width, specifically including all values within these ranges and any ranges created thereby. In such forms, areas of the article outside of the target zone 330 may be sans the substituted cyclodextrin complex. Or in other forms, the target zone 330 may comprise more substituted cyclodextrin complex than either of the outer zones 335.

In the case of catamenial tampons the substituted cyclodextrin complex can be present on or in any component of the tampon, including the absorbent compressed pledget forming the tampon body, the overwrap, and the extraction cord. For example, it can be comprised in the tampon body, or on the tampon surface or, if an overwrap is present, on either surface of the overwrap. In case a secondary mass of absorbent material is present along the extension cord proximal to the extraction end of the tampon, the substituted cyclodextrin complex can be comprised within this secondary mass.

In all cases, the substituted cyclodextrin complex of the invention can be applied on one of the layers making up the absorbent article in powder form or can be incorporated into a liquid or semi-solid carrier and applied as a lotion. In this case, the substituted cyclodextrin complexes can be dispersed in a carrier to form a dispersion, and the dispersion applied to the absorbent article. The carrier can be selected for example from the group consisting of polysiloxane oil, mineral oil, petrolatum, polyethylene glycol, glycerin and the like, and mixtures thereof. The carrier is preferably polysiloxane oil, such as a silicone glycol copolymer (commercially available from Dow Corning as Dow Corning 190 Fluid).

As stated previously, the odor control composition of the present disclosure can be provided in any suitable location or locations on a disposable absorbent article. However, it is believed that for those processes which involve spraying of the odor control complex onto one or more layers of the disposable absorbent article, can lead to contamination where the odor control complex is applied to some layers. For example, topsheets, as they are designed for quick fluid acquisition, may be permeable to such an extent that when spraying the odor control composition onto the topsheet, a portion of the odor control composition may pass through the topsheet onto the production equipment thereby causing contamination of the production line. Similarly, secondary topsheets may be designed such that they are permeable to such an extent that a portion of the sprayed odor control composition would blow through the secondary topsheet.

In contrast, the absorbent core is often the densest layer of the disposable absorbent article. It is therefore believed that where the odor control composition is sprayed onto the absorbent core, there is a much lower likelihood of a portion of the odor control composition blowing through the layer. So, in some forms, the odor control composition of the present disclosure may be provided on the absorbent core.

It is worth noting that additional optional layers may be provided between the topsheet and the absorbent core and/or between the backsheet and the absorbent core. So, the aqueous odor control composition of the present disclosure may be applied to one or more of the layers that make up the disposable absorbent article.

Other mechanisms of application of the odor control composition are contemplated. Additionally, the odor control composition of the present disclosure may be applied to AGM in the absorbent core as disclosed in US2018/033515. Additionally, where manufacturers of absorbent articles obtain webs of material from suppliers, the provision of the odor control composition may be provided by the supplier of the material. For example, an absorbent core supplier may apply the odor control composition to the absorbent core raw material. The absorbent core raw material may then be subsequently converted by the absorbent article manufacturer. Independently or in conjunction therewith, topsheet suppliers, secondary topsheet suppliers, or other raw material suppliers may apply the odor control composition of the present disclosure to raw materials for subsequent converting into absorbent articles.

The odor control composition of the present disclosure is aqueous during application to the disposable absorbent article and/or the layers which make up the disposable absorbent article. Disposable absorbent article manufacturers may obtain the aqueous odor control composition from a supplier, or the manufacturer may produce the odor control composition themselves.

Extraction of mBCD from Absorbent Articles mBCD can be collected from whole articles or components by Soxhlet extraction with water and the subsequent removal of solvent (water) using a rotary-evaporator. For further analysis of methyl substitution, enough articles need to be extracted to collect 50 mg of mBCD.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A disposable absorbent article comprising a topsheet, a backsheet, and an absorbent core disposed between the topsheet and the backsheet, the disposable absorbent article further comprising:
   an odor control composition comprising a preservative, a surfactant, perfume, and position-specific-substituted beta-cyclodextrin, having a degree of substitution in position 3 less than the level of substitution in position 2 and/or in position 6.

2. The disposable absorbent article of claim 1, wherein the odor control composition comprises from between from about 0.5 percent to 2.0 percent by weight of a preservative.

3. The disposable absorbent article of claim 1, wherein the odor control composition comprises from about 0.3 percent to about 2.0 percent by weight of a cyclodextrin-compatible surfactant.

4. The disposable absorbent article of claim 1, wherein the preservative comprises a compound represented by the following Structure I:

$$HO-CH_2-CH_2-R \quad (I)$$

wherein R is a substituted or unsubstituted phenyl group or a substituted or unsubstituted phenoxy group.

5. The disposable absorbent article of claim 1, wherein the position-specific-substituted beta-cyclodextrin has a substitution degree (DS) of 0.4 to 2.5 —R substituents per glucose unit of cyclodextrin and wherein substitution in position 2 is between about 20 percent and about 90 percent, in position 6 is between about 20 percent and about 90 percent.

6. The disposable absorbent article of claim 5, wherein substitution in position 3 is less than 50 percent.

7. The disposable absorbent article of claim 5, wherein the substitution degree is between about 0.9 and about 2.4.

8. The disposable absorbent article of claim 5, wherein the substitution degree is between about 1.2 and about 2.2.

9. The disposable absorbent article of claim 5, wherein the position-specific-substituted beta-cyclodextrin is substituted with substituents selected from linear or branched C1-C5 saturated chain.

10. The disposable absorbent article of claim 5, wherein the position-specific-substituted beta-cyclodextrin is substituted with substituents selected from methyl and hydroxymethyl.

11. The disposable absorbent article of claim 1, wherein the absorbent article further comprises an overall length generally parallel to a Y-axis and an overall width parallel to an X-axis, wherein the odor control composition is provided in a target zone of the absorbent article.

12. The disposable absorbent article of claim 11, wherein the target zone is disposed between two outer zones, and wherein the target zone comprises more than about 20 percent to less than about 80 percent of an overall length of the absorbent article.

13. The disposable absorbent article of claim 11, wherein the target zone is disposed between two outer zones, and wherein the target zone comprises more than about 30 percent to less than about 70 percent of the overall length of the absorbent article.

14. The disposable absorbent article of claim 1, wherein the odor control composition is provided on the absorbent core.

15. The disposable absorbent article of claim 1, wherein the perfume comprises a carrier, and wherein the carrier comprises isopropyl myristate.

16. The disposable absorbent article of claim 3, wherein the cyclodextrin-compatible surfactant is polyalkyleneoxide polysiloxane having a structure according to formula (1):

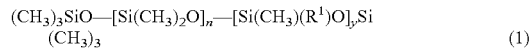

$$(CH_3)_3SiO-[Si(CH_3)_2O]_n-[Si(CH_3)(R^1)O]_b Si(CH_3)_3 \quad (1)$$

wherein a+b are from about 1 to about 50, and $R^1$ is the same or different and is selected from the group consisting of methyl and a poly(ethyleneoxide/propyleneoxide) copolymer groups having a structure according to formula (2);

$$—(CH_2)_nO(C_2H_4O)_c(C_3H_6O)_dR^2 \quad (2)$$

with at least one $R^1$ being a poly(ethyleneoxide (propyleneoxide) copolymer group, and wherein n is 3 or 4; total c (for all polyalkyleneoxy side groups) has a value of from 1 to about 100; d is from 0 to about 14; c+d has a value of from about 5 to about 150; and each $R^2$ is the same or different and is selected from the group consisting of hydrogen, an alkyl having 1 to 4 carbon atoms, and an acetyl group.

17. The disposable absorbent article of claim 1, wherein the perfume is present in an amount of from about 8 percent to about 10 percent.

18. The disposable absorbent article of claim 1, wherein the position-specific-substituted beta-cyclodextrin is present in an amount of from about 80 percent to about 90 percent.

19. A method of making a disposable absorbent article having an odor control composition, the method further comprising the steps of:

obtaining a topsheet material;

obtaining a backsheet material;

obtaining an absorbent core material;

placing the absorbent core material between the topsheet and the backsheet material;

obtaining one or more optional materials which are disposed between the topsheet and the absorbent core and/or the absorbent core and the backsheet;

obtaining an aqueous based odor control composition comprising a position-specific-substituted cyclodextrin, having a degree of substitution in position 3 less than the level of substitution in position 2 and/or in position 6, a preservative, a cyclodextrin compatible surfactant, and a perfume;

applying or having the aqueous based odor control composition applied to at least one of the topsheet, the backsheet, the absorbent core, or the optional materials.

20. The disposable absorbent article of claim 1, wherein the position-specific-substituted beta-cyclodextrin is substituted only with methyl substituents.

* * * * *